(12) United States Patent
Zollner et al.

(10) Patent No.: US 9,511,123 B2
(45) Date of Patent: *Dec. 6, 2016

(54) COMBINED USE OF A SULFATED GLYCOSAMINOGLYCAN AND A HYALURONIDASE FOR IMPROVING THE BIOAVAILABILITY OF FACTOR VIII

(71) Applicant: CSL BEHRING GMBH, Marburg (DE)

(72) Inventors: Sabine Zollner, Muri (CH); Hubert Metzner, Marburg (DE)

(73) Assignee: CSL Behring GmbH, Marburg (DE)

( * ) Notice: Subject to any disclaimer, the term of this patent is extended or adjusted under 35 U.S.C. 154(b) by 8 days.

This patent is subject to a terminal disclaimer.

(21) Appl. No.: 14/351,502

(22) PCT Filed: Oct. 18, 2012

(86) PCT No.: PCT/EP2012/070620
§ 371 (c)(1),
(2) Date: Apr. 11, 2014

(87) PCT Pub. No.: WO2013/057171
PCT Pub. Date: Apr. 25, 2013

(65) Prior Publication Data
US 2015/0023946 A1    Jan. 22, 2015

Related U.S. Application Data

(60) Provisional application No. 61/548,612, filed on Oct. 18, 2011.

(30) Foreign Application Priority Data

Oct. 18, 2011  (EP) ..................................... 11185850

(51) Int. Cl.
| | | |
|---|---|---|
| A61K 38/46 | (2006.01) | |
| A61K 38/37 | (2006.01) | |
| A61K 47/36 | (2006.01) | |
| A61K 38/47 | (2006.01) | |
| A61K 47/26 | (2006.01) | |
| A61K 31/727 | (2006.01) | |
| A61K 31/728 | (2006.01) | |

(52) U.S. Cl.
CPC ............. *A61K 38/37* (2013.01); *A61K 31/727* (2013.01); *A61K 31/728* (2013.01); *A61K 38/47* (2013.01); *A61K 47/26* (2013.01); *A61K 47/36* (2013.01); *C12Y 302/01025* (2013.01); *C12Y 302/01035* (2013.01)

(58) Field of Classification Search
CPC .. A61K 38/37; A61K 31/727; A61K 31/728; A61K 38/47; A61K 47/26; A61K 37/36; C12Y 302/01025
See application file for complete search history.

(56) References Cited

U.S. PATENT DOCUMENTS

| 4,757,006 A | 7/1988 | Toole, Jr. et al. |
| 4,868,112 A | 9/1989 | Toole, Jr. |
| 2002/0132306 A1 | 9/2002 | Kaufman et al. |
| 2005/0260186 A1 | 11/2005 | Bookbinder et al. |
| 2009/0247459 A1 | 10/2009 | Schwarz et al. |
| 2010/0143457 A1 | 6/2010 | Wei et al. |
| 2011/0189752 A1* | 8/2011 | Haberl et al. .................. 435/188 |
| 2014/0315815 A1 | 10/2014 | Metzner et al. |

FOREIGN PATENT DOCUMENTS

| EP | 0 503 991 A1 | 9/1992 |
| EP | 0 503 991 B1 | 9/1998 |
| EP | 0 784 632 B1 | 1/1999 |
| EP | 1 522 312 A1 | 4/2005 |
| WO | WO 95/01804 | 1/1995 |
| WO | WO 95/26750 | 10/1995 |
| WO | WO 97/40145 | 10/1997 |
| WO | WO 00/24759 | 5/2000 |
| WO | WO 00/77221 A1 | 12/2000 |
| WO | WO 02/102850 A2 | 12/2002 |
| WO | WO 2004/067566 A1 | 3/2004 |
| WO | WO 2004/101740 A2 | 11/2004 |
| WO | WO 2009/108806 A1 | 9/2009 |
| WO | WO 2010/077294 A1 | 7/2010 |
| WO | WO 2010/077297 A1 | 7/2010 |
| WO | WO 2011/020866 A2 | 2/2011 |
| WO | Wo 2011/095604 A1 | 8/2011 |

OTHER PUBLICATIONS

Definition of a kit. http://www.merriam-webster.com/dictionary/kit downloaded Nov. 16, 2015.*
Hirsch et al. (Circulation (1994) 89: 1449-1468.*
R. Kaufman, "Expression and Structure-Function Properties of Recombinant Factor VIII", Transfusion Medicine Reviews, vol. VI, No. 4, pp. 235-246 (1992).
B. Fischer at al., "Structural analysis of recombinant von Willebrand factor: identification of hetero- and homo-dimers", FEBS Letters 351, pp. 345-348 (1994).
Z. Ruggeri, "Structure and Function of von Willebrand Factor", Thrombosis and Haemostasis,, vol. 82, pp. 576-584 (1999).
C. Rizza et al., "Coagulation Assay of VIIIC and IXC", in Bloom ed. The Hemophilias, Churchill Livingston, NY, pp. 18-38 (1992).

(Continued)

*Primary Examiner* — Susan Hanley
(74) *Attorney, Agent, or Firm* — Finnegan, Henderson, Farabow, Garrett & Dunner LLP

(57) ABSTRACT

The present invention relates to pharmaceutical preparations comprising Factor VIII, a sulfated glycosaminoglycan and a hyaluronidase for the non-intravenous administration in the therapy and prophylactic treatment of bleeding disorders. The invention further relates to the combined use of a Factor VIII, a sulfated glycosaminoglycan and a hyaluronidase for the treatment and prevention of bleeding disorders, and to a method for increasing the bioavailability after non-intravenous administration of Factor VIII by co-administration of a sulfated glycosaminoglycan and a hyaluronidase.

5 Claims, 1 Drawing Sheet

(56) References Cited

OTHER PUBLICATIONS

S. Rosen, "Assay of Factor VIII:C with a Chromogenic Substrate", Scand J. Haematol, vol. 33, pp. 139-145 (1984).
K. Amano et al., "Mutation at either Arg336 or Arg562 in Factor VIII is insufficient for Complete Resistance to Activated Protein C (APC)-mediated inactivation: Implications for the APC Resistance Test", Thromb. Haemost, vol. 79, pp. 557-563 (1998).
M. Swaroop et al., "Mutagenesis of a Potential Immunoglobulin-binding Protein-binding Site Enhances Secretion of Coagulation Factor VIII", The Journal of Biological Chemistry, Vo. 272, No. 39, pp. 24121-24124 (1997).
P. Lollar, "Characterization of Factor VIII B-Cell Inhibitory Epitopes", Thrombosis and Haemostasis, vol. 82, pp. 505-508 (1999).
S. Oh et al., Sysnthesis of recombinant blood coagulation factor VIII (FVIII) heavy and light chains and reconstitution of active form of FVIII, Experimental and Molecular Medicine, vol. 31, No. 2, pp. 95-100 (1999).
N. Ananyeva et al., "Catabolism of the Coagulation Factor VIII", TCM, vol. 11, No. 6, pp. 251-257 (2001).
A. Gale et al., "Intrinsic stability and functional properties of disulfide bond-stabilized coagulation factor VIIIa variants" Journal of Thrombosis and Haemostasis, vol. 4, pp. 1315-1322 (2006).
H. Miao et al., "Bioengineering of coagulation factor VIII for improved secretion", Blood, vol. 103, No. 9, pp. 3412-3419 (2004).
H. Wakabayashi et al., "A Glu113Ala Mutation within a Factor VIII $Ca^{2+}$-Binding Site Enhances Cofactor Interactions in Factor Xase", Biochemistry, vol. 44, pp. 10928-10304 (2005).
S. Pipe, "Coagulation Factors with Improved Properties for Hemophilia Gene Therapy", Seminars in Thrombosis and Hemostasis. vol. 30, No. 2, pp. 227-237 (2004).
S. Krishnan et al., "Thrombin cleavage analysis of a novel anthihaemophilic factor variant, factor VIII Delta II", Eur. J. Biochem, vol. 195, pp. 637-644 (1991).
S. Herlitshka et al., "High expression of a B-domain deleted facor VIII gene in a human hepatic cell line", Journal of Biotechnology, vol. 61, pp 165-173 (1998).
M. Donath et al., "Characterization of des-(741-1668)-factor VIII, a single-chain factor VIII variant with a fusion site susceptible to proteolysis by thrombin and factor Xa", Biochem. J., Vo. 312, pp. 49-55 (1995).
J. Funderburgh, "Mini Review, Keratan sulfate: structure, biosynthesis, and function", Glycobiology, vol. 10, No. 10, pp. 951-958 (2000).
J. Gallagher et al., "Molecular structure of Heparan Sulfate and interactions with growth factors and morphogens". In Iozzo, M, V.. Proteoglycans: structure, biology and molecular interactions, pub. by Marcel Dekker Inc., New York, New York, pp. 27-59 (2000).
J. Gallagher et al., "Molecular distinctions between Heparan Sulphate and Heparin: Analysis of sulphation patterns indicates Heparan Sulphate and Heparin are separate families of N-sulphated polysaccharides". Biochem. J., vol. 230, pp. 665-674 (1985).
USP XXII-NF XVII, "Hyaluronidase for Injection", United States Pharmacopeial Convention, Inc, Rockville, MD, pp. 644-645 (1990).
W. Hynes et al., "Assays for hyaluronidase activity", Meth Enzymol, vol. 235, pp. 606-616 (1994).
G. Frost et al., "A Microtiter-Based Assay for Hyaluronidase Activity Not Requiring Specialized Reagents", Analytical Biochemistry, vol. 251, pp. 263-269 (1997).
B. Delpech et al., "Enzyme-Linked Hyaluronectin: A Unique Reagent for Hyaluronan Assay and Tissue Location and for Hyaluronidase Activity Detection", Analytical Biochemistry, vol. 229, pp. 35-41 (1995).
T. Takahashi et al., "A fluorimetric Norimetric Morgan-Elson assay method for hyaluronidase activity", Analytical Biochemistry, vol. 322, pp. 257-263 (2003).
L Bi et al., "Targeted disruption of the mouse factor VIII gene produces a model of haemophilia A", Nature genetics, vol, 10, pp. 119-121 (1995).
L Bi et al., "Further characterization of factor VIII-deficient mice created by gene targeting: RNA and protein studies", Blood, vol. 88, pp. 3446-3450 (1996).
D. Lillicrap, "Extending half-life in coagulation factors: where do we stand?" Thrombosis Research, vol. 122, pp. S2-S8 (2008).
L. Bookbinder et al., "A recombinant human enzyme for enhanced interstitial transport of therapeutics", Journal of Controlled Release, vol. 114, pp. 230-241 (2006).
International Search Report from the European Patent Office for International Application No. PCT/EP2012/070620 mailed Dec. 21, 2012.
Written Opinion of the International Search Authority from the European Patent Office for international Application No. PCT/EP2012/070620 mailed Dec. 21, 2012.
Extended European search report from the European Patent Office in corresponding EP 11 18 5650 from Munich, mailed Feb. 2, 2012.
First Examination Report issued on Jul. 15, 2014, in corresponding Australian application No. 2012318303, 3 pages.
Mio and Stern, "Inhibitors of the hyaluronidases." Matrix Biology (2002) 21:31-37.
Neufeld and Muenzer, "Chapter 136: The mucopolysaccarides." In: The Metabolic and Molecular Bases of Inherited Disease. Scriver et al. (eds.) (2001) 8th Edition, vol. III. McGraw-Hill, Medical Publishing Division.
Björkman, S., "Prophylactic Dosing of Factor VIII and Factor IX from a Clinical Pharmacokinetic Perspective." Haemophilia. 9(1):101-110 (2003).
Collins, P.W., et al., "Factor VIII requirement to maintain a target plasma level in the prophylactic treatment of severe hemophilia A: influences of variance in pharmacokinetics and treatment regimens", Journal of Thrombosis and Haemostasis, vol. 8, pp. 269-275 (2009).
HFA, Hemophilia Inheritance, http://www.hemophiliafed.org/bleeding-disorders/hemophilia/causes/, last visited May 1, 2015.
International Search Report issued by the European Patent Office in corresponding International Application No. PCT/EP2012/070615, mailed Dec. 12, 2012, 8 pages.
Notification Concerning Transmittal of International Report on Patentability and International Preliminary Report of Patentability, issued by The International Bureau of WIPO in International Application No. PCT/EP2012/070615, mailed May 1, 2014, 8 pages.
Shapiro, A.D., "Why is Primary Prophylaxis Underutilized in the United States?" Haemophilia. 9:670-672 (2003).
Shi, Q., et al., "Intravascular recovery of VWF and FVIII following intraperitoneal injection and differences from intravenous and subcutaneous injection in mice." Haemophilia. 18(4):639-646 (2012).
The Diagnosis, Evaluation, and Management of von Willebrand Factor Disease, NIH Publication No. 08-5832 Dec. 2007, p. 5, spanning col. 1-2.
Written Opinion of the International Searching Authority issued by the European Patent Office in corresponding International Application No. PCT/EP2012/070615, mailed Dec. 12, 2012, 14 pages.

\* cited by examiner

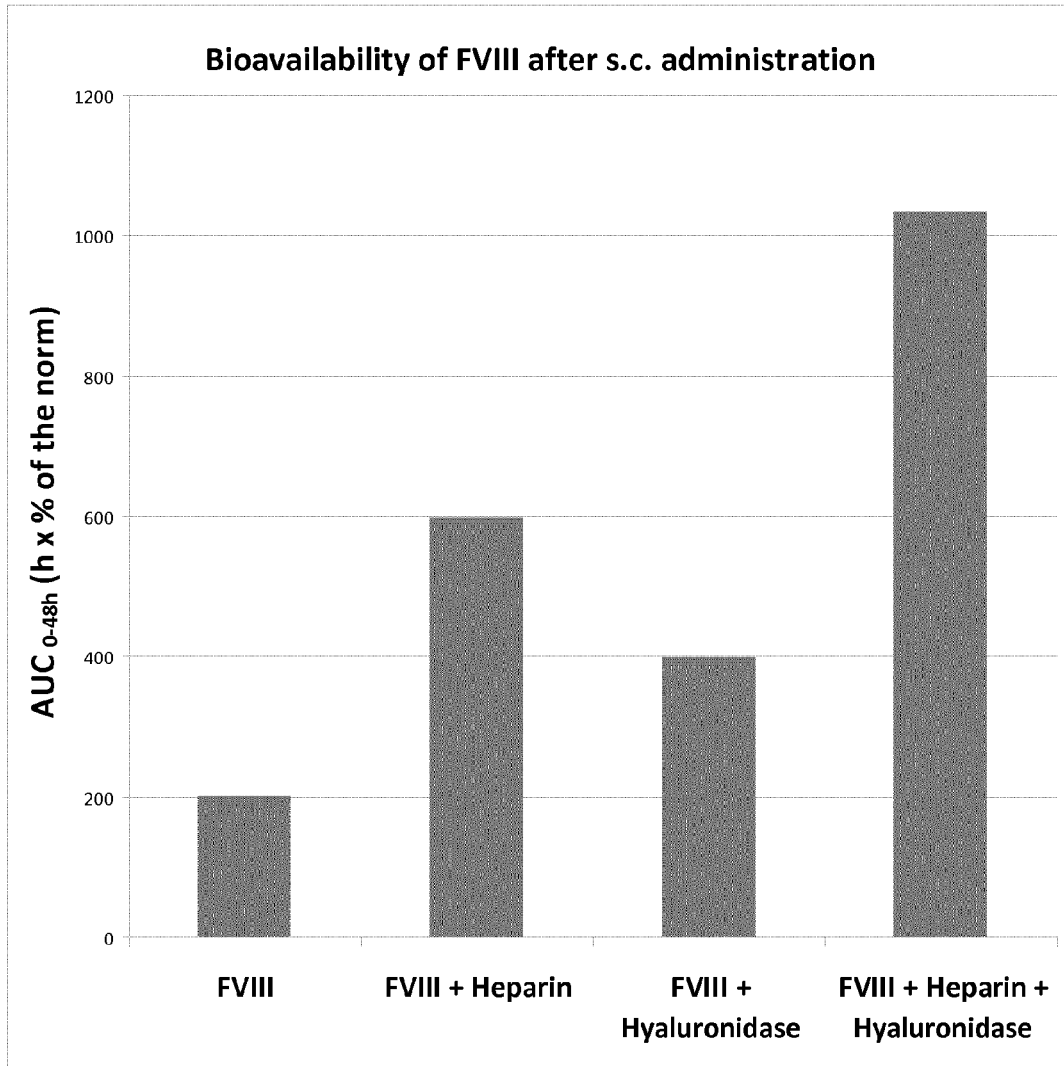

SEQUENCE LISTING

<160> NUMBER OF SEQ ID NOS: 2

<210> SEQ ID NO 1
<211> LENGTH: 6996
<212> TYPE: DNA
<213> ORGANISM: homo sapiens
<220> FEATURE:
<221> NAME/KEY: CDS
<222> LOCATION: (1)..(6996)

<400> SEQUENCE: 1

```
gcc acc aga aga tac tac ctg ggt gca gtg gaa ctg tca tgg gac tat     48
Ala Thr Arg Arg Tyr Tyr Leu Gly Ala Val Glu Leu Ser Trp Asp Tyr
1               5                   10                  15 atg caa agt gat ctc ggt gag ctg cct gtg gac gca aga ttt cct cct     96
Met Gln Ser Asp Leu Gly Glu Leu Pro Val Asp Ala Arg Phe Pro Pro
            20                  25                  30 aga gtg cca aaa tct ttt cca ttc aac acc tca gtc gtg tac aaa aag    144
Arg Val Pro Lys Ser Phe Pro Phe Asn Thr Ser Val Val Tyr Lys Lys
        35                  40                  45 act ctg ttt gta gaa ttc acg gat cac ctt ttc aac atc gct aag cca    192
Thr Leu Phe Val Glu Phe Thr Asp His Leu Phe Asn Ile Ala Lys Pro
    50                  55                  60 agg cca ccc tgg atg ggt ctg cta ggt cct acc atc cag gct gag gtt    240
Arg Pro Pro Trp Met Gly Leu Leu Gly Pro Thr Ile Gln Ala Glu Val
65                  70                  75                  80 tat gat aca gtg gtc att aca ctt aag aac atg gct tcc cat cct gtc    288
Tyr Asp Thr Val Val Ile Thr Leu Lys Asn Met Ala Ser His Pro Val
                85                  90                  95 agt ctt cat gct gtt ggt gta tcc tac tgg aaa gct tct gag gga gct    336
Ser Leu His Ala Val Gly Val Ser Tyr Trp Lys Ala Ser Glu Gly Ala
            100                 105                 110 gaa tat gat gat cag acc agt caa agg gag aaa gaa gat gat aaa gtc    384
Glu Tyr Asp Asp Gln Thr Ser Gln Arg Glu Lys Glu Asp Asp Lys Val
        115                 120                 125 ttc cct ggt gga agc cat aca tat gtc tgg cag gtc ctg aaa gag aat    432
Phe Pro Gly Gly Ser His Thr Tyr Val Trp Gln Val Leu Lys Glu Asn
    130                 135                 140 ggt cca atg gcc tct gac cca ctg tgc ctt acc tac tca tat ctt tct    480
Gly Pro Met Ala Ser Asp Pro Leu Cys Leu Thr Tyr Ser Tyr Leu Ser
145                 150                 155                 160 cat gtg gac ctg gta aaa gac ttg aat tca ggc ctc att gga gcc cta    528
His Val Asp Leu Val Lys Asp Leu Asn Ser Gly Leu Ile Gly Ala Leu
                165                 170                 175 cta gta tgt aga gaa ggg agt ctg gcc aag gaa aag aca cag acc ttg    576
Leu Val Cys Arg Glu Gly Ser Leu Ala Lys Glu Lys Thr Gln Thr Leu
            180                 185                 190 cac aaa ttt ata cta ctt ttt gct gta ttt gat gaa ggg aaa agt tgg    624
His Lys Phe Ile Leu Leu Phe Ala Val Phe Asp Glu Gly Lys Ser Trp
        195                 200                 205 cac tca gaa aca aag aac tcc ttg atg cag gat agg gat gct gca tct    672
His Ser Glu Thr Lys Asn Ser Leu Met Gln Asp Arg Asp Ala Ala Ser
    210                 215                 220 gct cgg gcc tgg cct aaa atg cac aca gtc aat ggt tat gta aac agg    720
Ala Arg Ala Trp Pro Lys Met His Thr Val Asn Gly Tyr Val Asn Arg
225                 230                 235                 240 tct ctg cca ggt ctg att gga tgc cac agg aaa tca gtc tat tgg cat    768
Ser Leu Pro Gly Leu Ile Gly Cys His Arg Lys Ser Val Tyr Trp His
                245                 250                 255 gtg att gga atg ggc acc act cct gaa gtg cac tca ata ttc ctc gaa    816
Val Ile Gly Met Gly Thr Thr Pro Glu Val His Ser Ile Phe Leu Glu
            260                 265                 270 ggt cac aca ttt ctt gtg agg aac cat cgc cag gcg tcc ttg gaa atc    864
Gly His Thr Phe Leu Val Arg Asn His Arg Gln Ala Ser Leu Glu Ile
        275                 280                 285 tcg cca ata act ttc ctt act gct caa aca ctc ttg atg gac ctt gga    912
Ser Pro Ile Thr Phe Leu Thr Ala Gln Thr Leu Leu Met Asp Leu Gly
    290                 295                 300
```

```
                                              -continued cag ttt cta ctg ttt tgt cat atc tct tcc cac caa cat gat ggc atg      960
Gln Phe Leu Leu Phe Cys His Ile Ser Ser His Gln His Asp Gly Met
305                 310                 315                 320 gaa gct tat gtc aaa gta gac agc tgt cca gag gaa ccc caa cta cga     1008
Glu Ala Tyr Val Lys Val Asp Ser Cys Pro Glu Glu Pro Gln Leu Arg
                325                 330                 335 atg aaa aat aat gaa gaa gcg gaa gac tat gat gat gat ctt act gat     1056
Met Lys Asn Asn Glu Glu Ala Glu Asp Tyr Asp Asp Asp Leu Thr Asp
            340                 345                 350 tct gaa atg gat gtg gtc agg ttt gat gat gac aac tct cct tcc ttt     1104
Ser Glu Met Asp Val Val Arg Phe Asp Asp Asp Asn Ser Pro Ser Phe
        355                 360                 365 atc caa att cgc tca gtt gcc aag aag cat cct aaa act tgg gta cat     1152
Ile Gln Ile Arg Ser Val Ala Lys Lys His Pro Lys Thr Trp Val His
    370                 375                 380 tac att gct gct gaa gag gag gac tgg gac tat gct ccc tta gtc ctc     1200
Tyr Ile Ala Ala Glu Glu Glu Asp Trp Asp Tyr Ala Pro Leu Val Leu
385                 390                 395                 400 gcc ccc gat gac aga agt tat aaa agt caa tat ttg aac aat ggc cct     1248
Ala Pro Asp Asp Arg Ser Tyr Lys Ser Gln Tyr Leu Asn Asn Gly Pro
                405                 410                 415 cag cgg att ggt agg aag tac aaa aaa gtc cga ttt atg gca tac aca     1296
Gln Arg Ile Gly Arg Lys Tyr Lys Lys Val Arg Phe Met Ala Tyr Thr
            420                 425                 430 gat gaa acc ttt aag act cgt gaa gct att cag cat gaa tca gga atc     1344
Asp Glu Thr Phe Lys Thr Arg Glu Ala Ile Gln His Glu Ser Gly Ile
        435                 440                 445 ttg gga cct tta ctt tat ggg gaa gtt gga gac aca ctg ttg att ata     1392
Leu Gly Pro Leu Leu Tyr Gly Glu Val Gly Asp Thr Leu Leu Ile Ile
    450                 455                 460 ttt aag aat caa gca agc aga cca tat aac atc tac cct cac gga atc     1440
Phe Lys Asn Gln Ala Ser Arg Pro Tyr Asn Ile Tyr Pro His Gly Ile
465                 470                 475                 480 act gat gtc cgt cct ttg tat tca agg aga tta cca aaa ggt gta aaa     1488
Thr Asp Val Arg Pro Leu Tyr Ser Arg Arg Leu Pro Lys Gly Val Lys
                485                 490                 495 cat ttg aag gat ttt cca att ctg cca gga gaa ata ttc aaa tat aaa     1536
His Leu Lys Asp Phe Pro Ile Leu Pro Gly Glu Ile Phe Lys Tyr Lys
            500                 505                 510 tgg aca gtg act gta gaa gat ggg cca act aaa tca gat cct cgg tgc     1584
Trp Thr Val Thr Val Glu Asp Gly Pro Thr Lys Ser Asp Pro Arg Cys
        515                 520                 525 ctg acc cgc tat tac tct agt ttc gtt aat atg gag aga gat cta gct     1632
Leu Thr Arg Tyr Tyr Ser Ser Phe Val Asn Met Glu Arg Asp Leu Ala
    530                 535                 540 tca gga ctc att ggc cct ctc ctc atc tgc tac aaa gaa tct gta gat     1680
Ser Gly Leu Ile Gly Pro Leu Leu Ile Cys Tyr Lys Glu Ser Val Asp
545                 550                 555                 560 caa aga gga aac cag ata atg tca gac aag agg aat gtc atc ctg ttt     1728
Gln Arg Gly Asn Gln Ile Met Ser Asp Lys Arg Asn Val Ile Leu Phe
                565                 570                 575 tct gta ttt gat gag aac cga agc tgg tac ctc aca gag aat ata caa     1776
Ser Val Phe Asp Glu Asn Arg Ser Trp Tyr Leu Thr Glu Asn Ile Gln
            580                 585                 590 cgc ttt ctc ccc aat cca gct gga gtg cag ctt gag gat cca gag ttc     1824
Arg Phe Leu Pro Asn Pro Ala Gly Val Gln Leu Glu Asp Pro Glu Phe
        595                 600                 605 caa gcc tcc aac atc atg cac agc atc aat ggc tat gtt ttt gat agt     1872
Gln Ala Ser Asn Ile Met His Ser Ile Asn Gly Tyr Val Phe Asp Ser
    610                 615                 620
```

```
ttg cag ttg tca gtt tgt ttg cat gag gtg gca tac tgg tac att cta    1920
Leu Gln Leu Ser Val Cys Leu His Glu Val Ala Tyr Trp Tyr Ile Leu
625                 630                 635                 640 agc att gga gca cag act gac ttc ctt tct gtc ttc ttc tct gga tat    1968
Ser Ile Gly Ala Gln Thr Asp Phe Leu Ser Val Phe Phe Ser Gly Tyr
            645                 650                 655 acc ttc aaa cac aaa atg gtc tat gaa gac aca ctc acc cta ttc cca    2016
Thr Phe Lys His Lys Met Val Tyr Glu Asp Thr Leu Thr Leu Phe Pro
        660                 665                 670 ttc tca gga gaa act gtc ttc atg tcg atg gaa aac cca ggt cta tgg    2064
Phe Ser Gly Glu Thr Val Phe Met Ser Met Glu Asn Pro Gly Leu Trp
    675                 680                 685 att ctg ggg tgc cac aac tca gac ttt cgg aac aga ggc atg acc gcc    2112
Ile Leu Gly Cys His Asn Ser Asp Phe Arg Asn Arg Gly Met Thr Ala
690                 695                 700 tta ctg aag gtt tct agt tgt gac aag aac act ggt gat tat tac gag    2160
Leu Leu Lys Val Ser Ser Cys Asp Lys Asn Thr Gly Asp Tyr Tyr Glu
705                 710                 715                 720 gac agt tat gaa gat att tca gca tac ttg ctg agt aaa aac aat gcc    2208
Asp Ser Tyr Glu Asp Ile Ser Ala Tyr Leu Leu Ser Lys Asn Asn Ala
            725                 730                 735 att gaa cca aga agc ttc tcc cag aat tca aga cac cgt agc act agg    2256
Ile Glu Pro Arg Ser Phe Ser Gln Asn Ser Arg His Arg Ser Thr Arg
        740                 745                 750 caa aag caa ttt aat gcc acc aca att cca gaa aat gac ata gag aag    2304
Gln Lys Gln Phe Asn Ala Thr Thr Ile Pro Glu Asn Asp Ile Glu Lys
    755                 760                 765 act gac cct tgg ttt gca cac aga aca cct atg cct aaa ata caa aat    2352
Thr Asp Pro Trp Phe Ala His Arg Thr Pro Met Pro Lys Ile Gln Asn
770                 775                 780 gtc tcc tct agt gat ttg ttg atg ctc ttg cga cag agt cct act cca    2400
Val Ser Ser Ser Asp Leu Leu Met Leu Leu Arg Gln Ser Pro Thr Pro
785                 790                 795                 800 cat ggg cta tcc tta tct gat ctc caa gaa gcc aaa tat gag act ttt    2448
His Gly Leu Ser Leu Ser Asp Leu Gln Glu Ala Lys Tyr Glu Thr Phe
            805                 810                 815 tct gat gat cca tca cct gga gca ata gac agt aat aac agc ctg tct    2496
Ser Asp Asp Pro Ser Pro Gly Ala Ile Asp Ser Asn Asn Ser Leu Ser
        820                 825                 830 gaa atg aca cac ttc agg cca cag ctc cat cac agt ggg gac atg gta    2544
Glu Met Thr His Phe Arg Pro Gln Leu His His Ser Gly Asp Met Val
    835                 840                 845 ttt acc cct gag tca ggc ctc caa tta aga tta aat gag aaa ctg ggg    2592
Phe Thr Pro Glu Ser Gly Leu Gln Leu Arg Leu Asn Glu Lys Leu Gly
850                 855                 860 aca act gca gca aca gag ttg aag aaa ctt gat ttc aaa gtt tct agt    2640
Thr Thr Ala Ala Thr Glu Leu Lys Lys Leu Asp Phe Lys Val Ser Ser
865                 870                 875                 880 aca tca aat aat ctg att tca aca att cca tca gac aat ttg gca gca    2688
Thr Ser Asn Asn Leu Ile Ser Thr Ile Pro Ser Asp Asn Leu Ala Ala
            885                 890                 895 ggt act gat aat aca agt tcc tta gga ccc cca agt atg cca gtt cat    2736
Gly Thr Asp Asn Thr Ser Ser Leu Gly Pro Pro Ser Met Pro Val His
        900                 905                 910 tat gat agt caa tta gat acc act cta ttt ggc aaa aag tca tct ccc    2784
Tyr Asp Ser Gln Leu Asp Thr Thr Leu Phe Gly Lys Lys Ser Ser Pro
    915                 920                 925 ctt act gag tct ggt gga cct ctg agc ttg agt gaa gaa aat aat gat    2832
Leu Thr Glu Ser Gly Gly Pro Leu Ser Leu Ser Glu Glu Asn Asn Asp
```

```
                    930                 935                 940
tca aag ttg tta gaa tca ggt tta atg aat agc caa gaa agt tca tgg    2880
Ser Lys Leu Leu Glu Ser Gly Leu Met Asn Ser Gln Glu Ser Ser Trp
945                 950                 955                 960 gga aaa aat gta tcg tca aca gag agt ggt agg tta ttt aaa ggg aaa    2928
Gly Lys Asn Val Ser Ser Thr Glu Ser Gly Arg Leu Phe Lys Gly Lys
                965                 970                 975 aga gct cat gga cct gct ttg ttg act aaa gat aat gcc tta ttc aaa    2976
Arg Ala His Gly Pro Ala Leu Leu Thr Lys Asp Asn Ala Leu Phe Lys
            980                 985                 990 gtt agc atc tct ttg tta aag aca aac aaa act tcc aat aat tca gca    3024
Val Ser Ile Ser Leu Leu Lys Thr Asn Lys Thr Ser Asn Asn Ser Ala
        995                 1000                1005 act aat aga aag act cac att gat ggc cca tca tta tta att gag        3069
Thr Asn Arg Lys Thr His Ile Asp Gly Pro Ser Leu Leu Ile Glu
    1010                1015                1020 aat agt cca tca gtc tgg caa aat ata tta gaa agt gac act gag        3114
Asn Ser Pro Ser Val Trp Gln Asn Ile Leu Glu Ser Asp Thr Glu
1025                1030                1035 ttt aaa aaa gtg aca cct ttg att cat gac aga atg ctt atg gac        3159
Phe Lys Lys Val Thr Pro Leu Ile His Asp Arg Met Leu Met Asp
            1040                1045                1050 aaa aat gct aca gct ttg agg cta aat cat atg tca aat aaa act        3204
Lys Asn Ala Thr Ala Leu Arg Leu Asn His Met Ser Asn Lys Thr
        1055                1060                1065 act tca tca aaa aac atg gaa atg gtc caa cag aaa aaa gag ggc        3249
Thr Ser Ser Lys Asn Met Glu Met Val Gln Gln Lys Lys Glu Gly
    1070                1075                1080 ccc att cca cca gat gca caa aat cca gat atg tcg ttc ttt aag        3294
Pro Ile Pro Pro Asp Ala Gln Asn Pro Asp Met Ser Phe Phe Lys
1085                1090                1095 atg cta ttc ttg cca gaa tca gca agg tgg ata caa agg act cat        3339
Met Leu Phe Leu Pro Glu Ser Ala Arg Trp Ile Gln Arg Thr His
            1100                1105                1110 gga aag aac tct ctg aac tct ggg caa ggc ccc agt cca aag caa        3384
Gly Lys Asn Ser Leu Asn Ser Gly Gln Gly Pro Ser Pro Lys Gln
        1115                1120                1125 tta gta tcc tta gga cca gaa aaa tct gtg gaa ggt cag aat ttc        3429
Leu Val Ser Leu Gly Pro Glu Lys Ser Val Glu Gly Gln Asn Phe
    1130                1135                1140 ttg tct gag aaa aac aaa gtg gta gta gga aag ggt gaa ttt aca        3474
Leu Ser Glu Lys Asn Lys Val Val Val Gly Lys Gly Glu Phe Thr
1145                1150                1155 aag gac gta gga ctc aaa gag atg gtt ttt cca agc agc aga aac        3519
Lys Asp Val Gly Leu Lys Glu Met Val Phe Pro Ser Ser Arg Asn
            1160                1165                1170 cta ttt ctt act aac ttg gat aat tta cat gaa aat aat aca cac        3564
Leu Phe Leu Thr Asn Leu Asp Asn Leu His Glu Asn Asn Thr His
        1175                1180                1185 aat caa gaa aaa aaa att cag gaa gaa ata gaa aag aag gaa aca        3609
Asn Gln Glu Lys Lys Ile Gln Glu Glu Ile Glu Lys Lys Glu Thr
    1190                1195                1200 tta atc caa gag aat gta gtt ttg cct cag ata cat aca gtg act        3654
Leu Ile Gln Glu Asn Val Val Leu Pro Gln Ile His Thr Val Thr
1205                1210                1215 ggc act aag aat ttc atg aag aac ctt ttc tta ctg agc act agg        3699
Gly Thr Lys Asn Phe Met Lys Asn Leu Phe Leu Leu Ser Thr Arg
            1220                1225                1230 caa aat gta gaa ggt tca tat gac ggg gca tat gct cca gta ctt        3744
```

-continued

| | | | | | | | | | | | | |
|---|---|---|---|---|---|---|---|---|---|---|---|---|
| Gln | Asn | Val | Glu | Gly | Ser | Tyr | Asp | Gly | Ala | Tyr | Ala | Pro | Val | Leu |
| 1235 | | | | | 1240 | | | | | 1245 | | | | |

```
caa gat ttt agg tca tta aat gat tca aca aat aga aca aag aaa      3789
Gln Asp Phe Arg Ser Leu Asn Asp Ser Thr Asn Arg Thr Lys Lys
1250                    1255                    1260 cac aca gct cat ttc tca aaa aaa ggg gag gaa gaa aac ttg gaa      3834
His Thr Ala His Phe Ser Lys Lys Gly Glu Glu Glu Asn Leu Glu
1265                    1270                    1275 ggc ttg gga aat caa acc aag caa att gta gag aaa tat gca tgc      3879
Gly Leu Gly Asn Gln Thr Lys Gln Ile Val Glu Lys Tyr Ala Cys
     1280                    1285                    1290 acc aca agg ata tct cct aat aca agc cag cag aat ttt gtc acg      3924
Thr Thr Arg Ile Ser Pro Asn Thr Ser Gln Gln Asn Phe Val Thr
1295                    1300                    1305 caa cgt agt aag aga gct ttg aaa caa ttc aga ctc cca cta gaa      3969
Gln Arg Ser Lys Arg Ala Leu Lys Gln Phe Arg Leu Pro Leu Glu
1310                    1315                    1320 gaa aca gaa ctt gaa aaa agg ata att gtg gat gac acc tca acc      4014
Glu Thr Glu Leu Glu Lys Arg Ile Ile Val Asp Asp Thr Ser Thr
1325                    1330                    1335 cag tgg tcc aaa aac atg aaa cat ttg acc ccg agc acc ctc aca      4059
Gln Trp Ser Lys Asn Met Lys His Leu Thr Pro Ser Thr Leu Thr
1340                    1345                    1350 cag ata gac tac aat gag aag gag aaa ggg gcc att act cag tct      4104
Gln Ile Asp Tyr Asn Glu Lys Glu Lys Gly Ala Ile Thr Gln Ser
1355                    1360                    1365 ccc tta tca gat tgc ctt acg agg agt cat agc atc cct caa gca      4149
Pro Leu Ser Asp Cys Leu Thr Arg Ser His Ser Ile Pro Gln Ala
1370                    1375                    1380 aat aga tct cca tta ccc att gca aag gta tca tca ttt cca tct      4194
Asn Arg Ser Pro Leu Pro Ile Ala Lys Val Ser Ser Phe Pro Ser
1385                    1390                    1395 att aga cct ata tat ctg acc agg gtc cta ttc caa gac aac tct      4239
Ile Arg Pro Ile Tyr Leu Thr Arg Val Leu Phe Gln Asp Asn Ser
1400                    1405                    1410 tct cat ctt cca gca gca tct tat aga aag aaa gat tct ggg gtc      4284
Ser His Leu Pro Ala Ala Ser Tyr Arg Lys Lys Asp Ser Gly Val
1415                    1420                    1425 caa gaa agc agt cat ttc tta caa gga gcc aaa aaa aat aac ctt      4329
Gln Glu Ser Ser His Phe Leu Gln Gly Ala Lys Lys Asn Asn Leu
1430                    1435                    1440 tct tta gcc att cta acc ttg gag atg act ggt gat caa aga gag      4374
Ser Leu Ala Ile Leu Thr Leu Glu Met Thr Gly Asp Gln Arg Glu
1445                    1450                    1455 gtt ggc tcc ctg ggg aca agt gcc aca aat tca gtc aca tac aag      4419
Val Gly Ser Leu Gly Thr Ser Ala Thr Asn Ser Val Thr Tyr Lys
1460                    1465                    1470 aaa gtt gag aac act gtt ctc ccg aaa cca gac ttg ccc aaa aca      4464
Lys Val Glu Asn Thr Val Leu Pro Lys Pro Asp Leu Pro Lys Thr
1475                    1480                    1485 tct ggc aaa gtt gaa ttg ctt cca aaa gtt cac att tat cag aag      4509
Ser Gly Lys Val Glu Leu Leu Pro Lys Val His Ile Tyr Gln Lys
1490                    1495                    1500 gac cta ttc cct acg gaa act agc aat ggg tct cct ggc cat ctg      4554
Asp Leu Phe Pro Thr Glu Thr Ser Asn Gly Ser Pro Gly His Leu
1505                    1510                    1515 gat ctc gtg gaa ggg agc ctt ctt cag gga aca gag gga gcg att      4599
Asp Leu Val Glu Gly Ser Leu Leu Gln Gly Thr Glu Gly Ala Ile
1520                    1525                    1530
```

| | | | | | | | | | | | |
|---|---|---|---|---|---|---|---|---|---|---|---|
| aag | tgg | aat | gaa | gca | aac | aga | cct | gga | aaa | gtt | ccc | ttt | ctg | aga | 4644 |
| Lys | Trp | Asn | Glu | Ala | Asn | Arg | Pro | Gly | Lys | Val | Pro | Phe | Leu | Arg | |
| 1535 | | | | 1540 | | | | | 1545 | | | | | | |

| gta | gca | aca | gaa | agc | tct | gca | aag | act | ccc | tcc | aag | cta | ttg | gat | 4689 |
| Val | Ala | Thr | Glu | Ser | Ser | Ala | Lys | Thr | Pro | Ser | Lys | Leu | Leu | Asp | |
| | 1550 | | | | 1555 | | | | 1560 | | | | | | |

| cct | ctt | gct | tgg | gat | aac | cac | tat | ggt | act | cag | ata | cca | aaa | gaa | 4734 |
| Pro | Leu | Ala | Trp | Asp | Asn | His | Tyr | Gly | Thr | Gln | Ile | Pro | Lys | Glu | |
| 1565 | | | | | 1570 | | | | | 1575 | | | | | |

| gag | tgg | aaa | tcc | caa | gag | aag | tca | cca | gaa | aaa | aca | gct | ttt | aag | 4779 |
| Glu | Trp | Lys | Ser | Gln | Glu | Lys | Ser | Pro | Glu | Lys | Thr | Ala | Phe | Lys | |
| | 1580 | | | | 1585 | | | | 1590 | | | | | | |

| aaa | aag | gat | acc | att | ttg | tcc | ctg | aac | gct | tgt | gaa | agc | aat | cat | 4824 |
| Lys | Lys | Asp | Thr | Ile | Leu | Ser | Leu | Asn | Ala | Cys | Glu | Ser | Asn | His | |
| 1595 | | | | | 1600 | | | | | 1605 | | | | | |

| gca | ata | gca | gca | ata | aat | gag | gga | caa | aat | aag | ccc | gaa | ata | gaa | 4869 |
| Ala | Ile | Ala | Ala | Ile | Asn | Glu | Gly | Gln | Asn | Lys | Pro | Glu | Ile | Glu | |
| 1610 | | | | | 1615 | | | | | 1620 | | | | | |

| gtc | acc | tgg | gca | aag | caa | ggt | agg | act | gaa | agg | ctg | tgc | tct | caa | 4914 |
| Val | Thr | Trp | Ala | Lys | Gln | Gly | Arg | Thr | Glu | Arg | Leu | Cys | Ser | Gln | |
| 1625 | | | | | 1630 | | | | | 1635 | | | | | |

| aac | cca | cca | gtc | ttg | aaa | cgc | cat | caa | cgg | gaa | ata | act | cgt | act | 4959 |
| Asn | Pro | Pro | Val | Leu | Lys | Arg | His | Gln | Arg | Glu | Ile | Thr | Arg | Thr | |
| 1640 | | | | | 1645 | | | | | 1650 | | | | | |

| act | ctt | cag | tca | gat | caa | gag | gaa | att | gac | tat | gat | gat | acc | ata | 5004 |
| Thr | Leu | Gln | Ser | Asp | Gln | Glu | Glu | Ile | Asp | Tyr | Asp | Asp | Thr | Ile | |
| 1655 | | | | | 1660 | | | | | 1665 | | | | | |

| tca | gtt | gaa | atg | aag | aag | gaa | gat | ttt | gac | att | tat | gat | gag | gat | 5049 |
| Ser | Val | Glu | Met | Lys | Lys | Glu | Asp | Phe | Asp | Ile | Tyr | Asp | Glu | Asp | |
| 1670 | | | | | 1675 | | | | | 1680 | | | | | |

| gaa | aat | cag | agc | ccc | cgc | agc | ttt | caa | aag | aaa | aca | cga | cac | tat | 5094 |
| Glu | Asn | Gln | Ser | Pro | Arg | Ser | Phe | Gln | Lys | Lys | Thr | Arg | His | Tyr | |
| 1685 | | | | | 1690 | | | | | 1695 | | | | | |

| ttt | att | gct | gca | gtg | gag | agg | ctc | tgg | gat | tat | ggg | atg | agt | agc | 5139 |
| Phe | Ile | Ala | Ala | Val | Glu | Arg | Leu | Trp | Asp | Tyr | Gly | Met | Ser | Ser | |
| 1700 | | | | | 1705 | | | | | 1710 | | | | | |

| tcc | cca | cat | gtt | cta | aga | aac | agg | gct | cag | agt | ggc | agt | gtc | cct | 5184 |
| Ser | Pro | His | Val | Leu | Arg | Asn | Arg | Ala | Gln | Ser | Gly | Ser | Val | Pro | |
| 1715 | | | | | 1720 | | | | | 1725 | | | | | |

| cag | ttc | aag | aaa | gtt | gtt | ttc | cag | gaa | ttt | act | gat | ggc | tcc | ttt | 5229 |
| Gln | Phe | Lys | Lys | Val | Val | Phe | Gln | Glu | Phe | Thr | Asp | Gly | Ser | Phe | |
| 1730 | | | | | 1735 | | | | | 1740 | | | | | |

| act | cag | ccc | tta | tac | cgt | gga | gaa | cta | aat | gaa | cat | ttg | gga | ctc | 5274 |
| Thr | Gln | Pro | Leu | Tyr | Arg | Gly | Glu | Leu | Asn | Glu | His | Leu | Gly | Leu | |
| 1745 | | | | | 1750 | | | | | 1755 | | | | | |

| ctg | ggg | cca | tat | ata | aga | gca | gaa | gtt | gaa | gat | aat | atc | atg | gta | 5319 |
| Leu | Gly | Pro | Tyr | Ile | Arg | Ala | Glu | Val | Glu | Asp | Asn | Ile | Met | Val | |
| 1760 | | | | | 1765 | | | | | 1770 | | | | | |

| act | ttc | aga | aat | cag | gcc | tct | cgt | ccc | tat | tcc | ttc | tat | tct | agc | 5364 |
| Thr | Phe | Arg | Asn | Gln | Ala | Ser | Arg | Pro | Tyr | Ser | Phe | Tyr | Ser | Ser | |
| 1775 | | | | | 1780 | | | | | 1785 | | | | | |

| ctt | att | tct | tat | gag | gaa | gat | cag | agg | caa | gga | gca | gaa | cct | aga | 5409 |
| Leu | Ile | Ser | Tyr | Glu | Glu | Asp | Gln | Arg | Gln | Gly | Ala | Glu | Pro | Arg | |
| 1790 | | | | | 1795 | | | | | 1800 | | | | | |

| aaa | aac | ttt | gtc | aag | cct | aat | gaa | acc | aaa | act | tac | ttt | tgg | aaa | 5454 |
| Lys | Asn | Phe | Val | Lys | Pro | Asn | Glu | Thr | Lys | Thr | Tyr | Phe | Trp | Lys | |
| 1805 | | | | | 1810 | | | | | 1815 | | | | | |

| gtg | caa | cat | cat | atg | gca | ccc | act | aaa | gat | gag | ttt | gac | tgc | aaa | 5499 |
| Val | Gln | His | His | Met | Ala | Pro | Thr | Lys | Asp | Glu | Phe | Asp | Cys | Lys | |
| 1820 | | | | | 1825 | | | | | 1830 | | | | | |

```
gcc tgg gct tat ttc tct gat gtt gac ctg gaa aaa gat gtg cac      5544
Ala Trp Ala Tyr Phe Ser Asp Val Asp Leu Glu Lys Asp Val His
1835                1840                1845 tca ggc ctg att gga ccc ctt ctg gtc tgc cac act aac aca ctg      5589
Ser Gly Leu Ile Gly Pro Leu Leu Val Cys His Thr Asn Thr Leu
    1850                1855                1860 aac cct gct cat ggg aga caa gtg aca gta cag gaa ttt gct ctg      5634
Asn Pro Ala His Gly Arg Gln Val Thr Val Gln Glu Phe Ala Leu
1865                1870                1875 ttt ttc acc atc ttt gat gag acc aaa agc tgg tac ttc act gaa      5679
Phe Phe Thr Ile Phe Asp Glu Thr Lys Ser Trp Tyr Phe Thr Glu
    1880                1885                1890 aat atg gaa aga aac tgc agg gct ccc tgc aat atc cag atg gaa      5724
Asn Met Glu Arg Asn Cys Arg Ala Pro Cys Asn Ile Gln Met Glu
1895                1900                1905 gat ccc act ttt aaa gag aat tat cgc ttc cat gca atc aat ggc      5769
Asp Pro Thr Phe Lys Glu Asn Tyr Arg Phe His Ala Ile Asn Gly
    1910                1915                1920 tac ata atg gat aca cta cct ggc tta gta atg gct cag gat caa      5814
Tyr Ile Met Asp Thr Leu Pro Gly Leu Val Met Ala Gln Asp Gln
1925                1930                1935 agg att cga tgg tat ctg ctc agc atg ggc agc aat gaa aac atc      5859
Arg Ile Arg Trp Tyr Leu Leu Ser Met Gly Ser Asn Glu Asn Ile
    1940                1945                1950 cat tct att cat ttc agt gga cat gtg ttc act gta cga aaa aaa      5904
His Ser Ile His Phe Ser Gly His Val Phe Thr Val Arg Lys Lys
1955                1960                1965 gag gag tat aaa atg gca ctg tac aat ctc tat cca ggt gtt ttt      5949
Glu Glu Tyr Lys Met Ala Leu Tyr Asn Leu Tyr Pro Gly Val Phe
    1970                1975                1980 gag aca gtg gaa atg tta cca tcc aaa gct gga att tgg cgg gtg      5994
Glu Thr Val Glu Met Leu Pro Ser Lys Ala Gly Ile Trp Arg Val
1985                1990                1995 gaa tgc ctt att ggc gag cat cta cat gct ggg atg agc aca ctt      6039
Glu Cys Leu Ile Gly Glu His Leu His Ala Gly Met Ser Thr Leu
2000                2005                2010 ttt ctg gtg tac agc aat aag tgt cag act ccc ctg gga atg gct      6084
Phe Leu Val Tyr Ser Asn Lys Cys Gln Thr Pro Leu Gly Met Ala
    2015                2020                2025 tct gga cac att aga gat ttt cag att aca gct tca gga caa tat      6129
Ser Gly His Ile Arg Asp Phe Gln Ile Thr Ala Ser Gly Gln Tyr
2030                2035                2040 gga cag tgg gcc cca aag ctg gcc aga ctt cat tat tcc gga tca      6174
Gly Gln Trp Ala Pro Lys Leu Ala Arg Leu His Tyr Ser Gly Ser
    2045                2050                2055 atc aat gcc tgg agc acc aag gag ccc ttt tct tgg atc aag gtg      6219
Ile Asn Ala Trp Ser Thr Lys Glu Pro Phe Ser Trp Ile Lys Val
2060                2065                2070 gat ctg ttg gca cca atg att att cac ggc atc aag acc cag ggt      6264
Asp Leu Leu Ala Pro Met Ile Ile His Gly Ile Lys Thr Gln Gly
    2075                2080                2085 gcc cgt cag aag ttc tcc agc ctc tac atc tct cag ttt atc atc      6309
Ala Arg Gln Lys Phe Ser Ser Leu Tyr Ile Ser Gln Phe Ile Ile
2090                2095                2100 atg tat agt ctt gat ggg aag aag tgg cag act tat cga gga aat      6354
Met Tyr Ser Leu Asp Gly Lys Lys Trp Gln Thr Tyr Arg Gly Asn
    2105                2110                2115 tcc act gga acc tta atg gtc ttc ttt ggc aat gtg gat tca tct      6399
Ser Thr Gly Thr Leu Met Val Phe Phe Gly Asn Val Asp Ser Ser
```

```
                2120                2125                2130
ggg ata aaa cac aat att ttt aac cct cca att att gct cga tac       6444
Gly Ile Lys His Asn Ile Phe Asn Pro Pro Ile Ile Ala Arg Tyr
    2135                2140                2145 atc cgt ttg cac cca act cat tat agc att cgc agc act ctt cgc       6489
Ile Arg Leu His Pro Thr His Tyr Ser Ile Arg Ser Thr Leu Arg
2150                2155                2160 atg gag ttg atg ggc tgt gat tta aat agt tgc agc atg cca ttg       6534
Met Glu Leu Met Gly Cys Asp Leu Asn Ser Cys Ser Met Pro Leu
    2165                2170                2175 gga atg gag agt aaa gca ata tca gat gca cag att act gct tca       6579
Gly Met Glu Ser Lys Ala Ile Ser Asp Ala Gln Ile Thr Ala Ser
2180                2185                2190 tcc tac ttt acc aat atg ttt gcc acc tgg tct cct tca aaa gct       6624
Ser Tyr Phe Thr Asn Met Phe Ala Thr Trp Ser Pro Ser Lys Ala
    2195                2200                2205 cga ctt cac ctc caa ggg agg agt aat gcc tgg aga cct cag gtg       6669
Arg Leu His Leu Gln Gly Arg Ser Asn Ala Trp Arg Pro Gln Val
2210                2215                2220 aat aat cca aaa gag tgg ctg caa gtg gac ttc cag aag aca atg       6714
Asn Asn Pro Lys Glu Trp Leu Gln Val Asp Phe Gln Lys Thr Met
    2225                2230                2235 aaa gtc aca gga gta act act cag gga gta aaa tct ctg ctt acc       6759
Lys Val Thr Gly Val Thr Thr Gln Gly Val Lys Ser Leu Leu Thr
2240                2245                2250 agc atg tat gtg aag gag ttc ctc atc tcc agc agt caa gat ggc       6804
Ser Met Tyr Val Lys Glu Phe Leu Ile Ser Ser Ser Gln Asp Gly
    2255                2260                2265 cat cag tgg act ctc ttt ttt cag aat ggc aaa gta aag gtt ttt       6849
His Gln Trp Thr Leu Phe Phe Gln Asn Gly Lys Val Lys Val Phe
2270                2275                2280 cag gga aat caa gac tcc ttc aca cct gtg gtg aac tct cta gac       6894
Gln Gly Asn Gln Asp Ser Phe Thr Pro Val Val Asn Ser Leu Asp
    2285                2290                2295 cca ccg tta ctg act cgc tac ctt cga att cac ccc cag agt tgg       6939
Pro Pro Leu Leu Thr Arg Tyr Leu Arg Ile His Pro Gln Ser Trp
2300                2305                2310 gtg cac cag att gcc ctg agg atg gag gtt ctg ggc tgc gag gca       6984
Val His Gln Ile Ala Leu Arg Met Glu Val Leu Gly Cys Glu Ala
    2315                2320                2325 cag gac ctc tac                                                    6996
Gln Asp Leu Tyr
2330
```

<210> SEQ ID NO 2
<211> LENGTH: 2332
<212> TYPE: PRT
<213> ORGANISM: homo sapiens

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val

```
                65                  70                  75                  80
Tyr Asp Thr Val Val Ile Thr Leu Lys Asn Met Ala Ser His Pro Val
                    85                  90                  95
Ser Leu His Ala Val Gly Val Ser Tyr Trp Lys Ala Ser Glu Gly Ala
                    100                 105                 110
Glu Tyr Asp Asp Gln Thr Ser Gln Arg Glu Lys Glu Asp Asp Lys Val
                    115                 120                 125
Phe Pro Gly Gly Ser His Thr Tyr Val Trp Gln Val Leu Lys Glu Asn
                130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                    165                 170                 175
Leu Val Cys Arg Glu Gly Ser Leu Ala Lys Lys Thr Gln Thr Leu
                    180                 185                 190
His Lys Phe Ile Leu Leu Phe Ala Val Phe Asp Glu Gly Lys Ser Trp
                195                 200                 205
His Ser Glu Thr Lys Asn Ser Leu Met Gln Asp Arg Asp Ala Ala Ser
                210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                    245                 250                 255
Val Ile Gly Met Gly Thr Thr Pro Glu Val His Ser Ile Phe Leu Glu
                    260                 265                 270
Gly His Thr Phe Leu Val Arg Asn His Arg Gln Ala Ser Leu Glu Ile
                    275                 280                 285
Ser Pro Ile Thr Phe Leu Thr Ala Gln Thr Leu Leu Met Asp Leu Gly
                    290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                    325                 330                 335
Met Lys Asn Asn Glu Glu Ala Glu Asp Tyr Asp Asp Asp Leu Thr Asp
                    340                 345                 350
Ser Glu Met Asp Val Val Arg Phe Asp Asp Asn Ser Pro Ser Phe
                355                 360                 365
Ile Gln Ile Arg Ser Val Ala Lys Lys His Pro Lys Thr Trp Val His
                370                 375                 380
Tyr Ile Ala Ala Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                    405                 410                 415
Gln Arg Ile Gly Arg Lys Tyr Lys Lys Val Arg Phe Met Ala Tyr Thr
                    420                 425                 430
Asp Glu Thr Phe Lys Thr Arg Glu Ala Ile Gln His Glu Ser Gly Ile
                435                 440                 445
Leu Gly Pro Leu Leu Tyr Gly Glu Val Gly Asp Thr Leu Leu Ile Ile
                450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                    485                 490                 495
```

```
His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Arg Ser Thr Arg
            740                 745                 750

Gln Lys Gln Phe Asn Ala Thr Thr Ile Pro Glu Asn Asp Ile Glu Lys
            755                 760                 765

Thr Asp Pro Trp Phe Ala His Arg Thr Pro Met Pro Lys Ile Gln Asn
            770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
            835                 840                 845

Phe Thr Pro Glu Ser Gly Leu Gln Leu Arg Leu Asn Glu Lys Leu Gly
            850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910
```

-continued

```
Tyr Asp Ser Gln Leu Asp Thr Thr Leu Phe Gly Lys Lys Ser Ser Pro
    915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

Gln Asn Val Glu Gly Ser Tyr Asp Gly Ala Tyr Ala Pro Val Leu
    1235                1240                1245

Gln Asp Phe Arg Ser Leu Asn Asp Ser Thr Asn Arg Thr Lys Lys
    1250                1255                1260

His Thr Ala His Phe Ser Lys Lys Gly Glu Glu Glu Asn Leu Glu
    1265                1270                1275

Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
    1295                1300                1305

Gln Arg Ser Lys Arg Ala Leu Lys Gln Phe Arg Leu Pro Leu Glu
```

-continued

```
              1310                1315                1320
Glu  Thr  Glu  Leu  Glu  Lys  Arg  Ile  Ile  Val  Asp  Asp  Thr  Ser  Thr
              1325                1330                1335
Gln  Trp  Ser  Lys  Asn  Met  Lys  His  Leu  Thr  Pro  Ser  Thr  Leu  Thr
              1340                1345                1350
Gln  Ile  Asp  Tyr  Asn  Glu  Lys  Glu  Lys  Gly  Ala  Ile  Thr  Gln  Ser
              1355                1360                1365
Pro  Leu  Ser  Asp  Cys  Leu  Thr  Arg  Ser  His  Ser  Ile  Pro  Gln  Ala
              1370                1375                1380
Asn  Arg  Ser  Pro  Leu  Pro  Ile  Ala  Lys  Val  Ser  Ser  Phe  Pro  Ser
              1385                1390                1395
Ile  Arg  Pro  Ile  Tyr  Leu  Thr  Arg  Val  Leu  Phe  Gln  Asp  Asn  Ser
              1400                1405                1410
Ser  His  Leu  Pro  Ala  Ala  Ser  Tyr  Arg  Lys  Lys  Asp  Ser  Gly  Val
              1415                1420                1425
Gln  Glu  Ser  Ser  His  Phe  Leu  Gln  Gly  Ala  Lys  Lys  Asn  Asn  Leu
              1430                1435                1440
Ser  Leu  Ala  Ile  Leu  Thr  Leu  Glu  Met  Thr  Gly  Asp  Gln  Arg  Glu
              1445                1450                1455
Val  Gly  Ser  Leu  Gly  Thr  Ser  Ala  Thr  Asn  Ser  Val  Thr  Tyr  Lys
              1460                1465                1470
Lys  Val  Glu  Asn  Thr  Val  Leu  Pro  Lys  Pro  Asp  Leu  Pro  Lys  Thr
              1475                1480                1485
Ser  Gly  Lys  Val  Glu  Leu  Leu  Pro  Lys  Val  His  Ile  Tyr  Gln  Lys
              1490                1495                1500
Asp  Leu  Phe  Pro  Thr  Glu  Thr  Ser  Asn  Gly  Ser  Pro  Gly  His  Leu
              1505                1510                1515
Asp  Leu  Val  Glu  Gly  Ser  Leu  Leu  Gln  Gly  Thr  Glu  Gly  Ala  Ile
              1520                1525                1530
Lys  Trp  Asn  Glu  Ala  Asn  Arg  Pro  Gly  Lys  Val  Pro  Phe  Leu  Arg
              1535                1540                1545
Val  Ala  Thr  Glu  Ser  Ser  Ala  Lys  Thr  Pro  Ser  Lys  Leu  Leu  Asp
              1550                1555                1560
Pro  Leu  Ala  Trp  Asp  Asn  His  Tyr  Gly  Thr  Gln  Ile  Pro  Lys  Glu
              1565                1570                1575
Glu  Trp  Lys  Ser  Gln  Glu  Lys  Ser  Pro  Glu  Lys  Thr  Ala  Phe  Lys
              1580                1585                1590
Lys  Lys  Asp  Thr  Ile  Leu  Ser  Leu  Asn  Ala  Cys  Glu  Ser  Asn  His
              1595                1600                1605
Ala  Ile  Ala  Ala  Ile  Asn  Glu  Gly  Gln  Asn  Lys  Pro  Glu  Ile  Glu
              1610                1615                1620
Val  Thr  Trp  Ala  Lys  Gln  Gly  Arg  Thr  Glu  Arg  Leu  Cys  Ser  Gln
              1625                1630                1635
Asn  Pro  Pro  Val  Leu  Lys  Arg  His  Gln  Arg  Glu  Ile  Thr  Arg  Thr
              1640                1645                1650
Thr  Leu  Gln  Ser  Asp  Gln  Glu  Glu  Ile  Asp  Tyr  Asp  Asp  Thr  Ile
              1655                1660                1665
Ser  Val  Glu  Met  Lys  Lys  Glu  Asp  Phe  Asp  Ile  Tyr  Asp  Glu  Asp
              1670                1675                1680
Glu  Asn  Gln  Ser  Pro  Arg  Ser  Phe  Gln  Lys  Lys  Thr  Arg  His  Tyr
              1685                1690                1695
Phe  Ile  Ala  Ala  Val  Glu  Arg  Leu  Trp  Asp  Tyr  Gly  Met  Ser  Ser
              1700                1705                1710
```

```
Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860

Asn Pro Ala His Gly Arg Gln Val Thr Val Gln Glu Phe Ala Leu
1865                1870                1875

Phe Phe Thr Ile Phe Asp Glu Thr Lys Ser Trp Tyr Phe Thr Glu
1880                1885                1890

Asn Met Glu Arg Asn Cys Arg Ala Pro Cys Asn Ile Gln Met Glu
1895                1900                1905

Asp Pro Thr Phe Lys Glu Asn Tyr Arg Phe His Ala Ile Asn Gly
1910                1915                1920

Tyr Ile Met Asp Thr Leu Pro Gly Leu Val Met Ala Gln Asp Gln
1925                1930                1935

Arg Ile Arg Trp Tyr Leu Leu Ser Met Gly Ser Asn Glu Asn Ile
1940                1945                1950

His Ser Ile His Phe Ser Gly His Val Phe Thr Val Arg Lys Lys
1955                1960                1965

Glu Glu Tyr Lys Met Ala Leu Tyr Asn Leu Tyr Pro Gly Val Phe
1970                1975                1980

Glu Thr Val Glu Met Leu Pro Ser Lys Ala Gly Ile Trp Arg Val
1985                1990                1995

Glu Cys Leu Ile Gly Glu His Leu His Ala Gly Met Ser Thr Leu
2000                2005                2010

Phe Leu Val Tyr Ser Asn Lys Cys Gln Thr Pro Leu Gly Met Ala
2015                2020                2025

Ser Gly His Ile Arg Asp Phe Gln Ile Thr Ala Ser Gly Gln Tyr
2030                2035                2040

Gly Gln Trp Ala Pro Lys Leu Ala Arg Leu His Tyr Ser Gly Ser
2045                2050                2055

Ile Asn Ala Trp Ser Thr Lys Glu Pro Phe Ser Trp Ile Lys Val
2060                2065                2070

Asp Leu Leu Ala Pro Met Ile Ile His Gly Ile Lys Thr Gln Gly
2075                2080                2085

Ala Arg Gln Lys Phe Ser Ser Leu Tyr Ile Ser Gln Phe Ile Ile
2090                2095                2100
```

-continued

```
Met Tyr Ser Leu Asp Gly Lys Lys Trp Gln Thr Tyr Arg Gly Asn
2105                2110                2115

Ser Thr Gly Thr Leu Met Val Phe Phe Gly Asn Val Asp Ser Ser
2120                2125                2130

Gly Ile Lys His Asn Ile Phe Asn Pro Pro Ile Ile Ala Arg Tyr
2135                2140                2145

Ile Arg Leu His Pro Thr His Tyr Ser Ile Arg Ser Thr Leu Arg
2150                2155                2160

Met Glu Leu Met Gly Cys Asp Leu Asn Ser Cys Ser Met Pro Leu
2165                2170                2175

Gly Met Glu Ser Lys Ala Ile Ser Asp Ala Gln Ile Thr Ala Ser
2180                2185                2190

Ser Tyr Phe Thr Asn Met Phe Ala Thr Trp Ser Pro Ser Lys Ala
2195                2200                2205

Arg Leu His Leu Gln Gly Arg Ser Asn Ala Trp Arg Pro Gln Val
2210                2215                2220

Asn Asn Pro Lys Glu Trp Leu Gln Val Asp Phe Gln Lys Thr Met
2225                2230                2235

Lys Val Thr Gly Val Thr Thr Gln Gly Val Lys Ser Leu Leu Thr
2240                2245                2250

Ser Met Tyr Val Lys Glu Phe Leu Ile Ser Ser Ser Gln Asp Gly
2255                2260                2265

His Gln Trp Thr Leu Phe Phe Gln Asn Gly Lys Val Lys Val Phe
2270                2275                2280

Gln Gly Asn Gln Asp Ser Phe Thr Pro Val Val Asn Ser Leu Asp
2285                2290                2295

Pro Pro Leu Leu Thr Arg Tyr Leu Arg Ile His Pro Gln Ser Trp
2300                2305                2310

Val His Gln Ile Ala Leu Arg Met Glu Val Leu Gly Cys Glu Ala
2315                2320                2325

Gln Asp Leu Tyr
2330
```

COMBINED USE OF A SULFATED GLYCOSAMINOGLYCAN AND A HYALURONIDASE FOR IMPROVING THE BIOAVAILABILITY OF FACTOR VIII

This application is a national phase entry of International Application No. PCT/EP2012/070620, filed on Oct. 18, 2012, and claims priority to U.S. Provisional Application No. 61/548,612, filed on Oct. 18, 2011, and also claims priority to European Application No. EP 11185650.6, filed on Oct. 18, 2011.

The present invention relates to pharmaceutical preparations comprising at least one Factor VIII, at least one sulfated glycosaminoglycan and at least one hyaluronidase for the non-intravenous administration in the therapy and prophylactic treatment of bleeding disorders. The invention further relates to the combined use of Factor VIII, a sulfated glycosaminoglycan and a hyaluronidase for the treatment and prevention of bleeding disorders, and to a method for increasing the bioavailability after non-intravenous administration of Factor VIII by co-administration of a sulfated glycosaminoglycan and a hyaluronidase.

BACKGROUND OF THE INVENTION

Factor VIII (FVIII)

FVIII is a blood plasma glycoprotein of about 280 kDa molecular mass, produced in the liver of mammals. It is a critical component of the cascade of coagulation reactions that lead to blood clotting. Within this cascade is a step in which factor IXa (FIXa), in conjunction with activated factor VIII (FVIIIa), converts factor X (FX) to an activated form, FXa. FVIIIa acts as a cofactor at this step, being required together with calcium ions and phospholipids for maximizing the activity of FIXa. The most common hemophilic disorder is caused by a deficiency of functional FVIII called hemophilia A.

An important advance in the treatment of Hemophilia A has been the isolation of cDNA clones encoding the complete 2,351 amino acid sequence of human FVIII (U.S. Pat. No. 4,757,006) and the provision of the human FVIII gene DNA sequence and recombinant methods for its production).

Analysis of the deduced primary amino acid sequence of human FVIII determined from the cloned cDNA indicates that it is a heterodimer processed from a larger precursor polypeptide. The heterodimer consists of a C-terminal light chain of about 80 kDa in a metal ion-dependent association with an about 200 kDa N-terminal heavy chain. (See review by Kaufman, Transfusion Med. Revs. 6:235 (1992)). Physiological activation of the heterodimer occurs through proteolytic cleavage of the protein chains by thrombin. Thrombin cleaves the heavy chain to a 90 kDa protein, and then to 54 kDa and 44 kDa fragments. Thrombin also cleaves the 80 kDa light chain into a 72 kDa protein. It is the latter protein, and the two heavy chain fragments (54 kDa and 44 kDa above), held together by calcium ions, that constitute active FVIII. Inactivation occurs when the 44 kDa A2 heavy chain fragment dissociates from the molecule or when the 72 kDa and 54 kDa domains are further cleaved by thrombin, activated protein C or FXa. In plasma, FVIII is stabilized by association with a 50-fold molar excess of Von Willebrand Factor protein ("VWF"), which appears to inhibit proteolytic destruction of FVIII as described above.

The amino acid sequence of FVIII is organized into three structural domains: a triplicated A domain of 330 amino acids, a single B domain of 980 amino acids, and a duplicated C domain of 150 amino acids. The B domain has no homology to other proteins and provides 18 of the 25 potential asparagine(N)-linked glycosylation sites of this protein. The B domain has apparently no function in coagulation and can be deleted with the B-domain deleted FVIII molecule still having procoagulatory activity.

Von Willebrand Factor (VWF)

VWF is a multimeric adhesive glycoprotein present in the plasma of mammals, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule. The precursor polypeptide, pre-pro-VWF, consists of a 22-residue signal peptide, a 741-residue pro-peptide and the 2050-residue polypeptide found in mature plasma VWF (Fischer et al., FEBS Lett. 351: 345-348, 1994). Upon secretion into plasma VWF circulates in the form of various species with different molecular sizes. These VWF molecules consist of oligo- and multimers of the mature subunit of 2050 amino acid residues. VWF can be usually found in plasma as one dimer up to multimers consisting of 50-100 dimers (Ruggeri et al. Thromb. Haemost. 82: 576-584, 1999). The in vivo half-life of human VWF in the human circulation is approximately 12 hours.

The most frequent inherited bleeding disorder in humans is von Willebrand's disease (VWD). Depending on the severity of the bleeding symptoms, VWD can be treated by replacement therapy with concentrates containing VWF, in general derived from human plasma but recombinant VWF also is under development. VWF can be prepared from human plasma as for example described in EP 0503991. In patent EP 0784632 a method for isolating recombinant VWF is described.

VWF is known to stabilize FVIII in vivo and, thus, plays a crucial role to regulate plasma levels of FVIII and as a consequence is a central factor to control primary and secondary hemostasis. It is also known that after intravenous administration of pharmaceutical preparations containing VWF in VWD patients an increase in endogenous FVIII:C to 1 to 3 units per ml in 24 hours can be observed demonstrating the in vivo stabilizing effect of VWF on FVIII.

The patients in general benefit from the specific mode of action of the active ingredients but currently all commercially available Factor VIII preparations are administered via intravenous administration which involves a risk for infections at the injection site and is in general a procedure patients would like to avoid especially in the treatment of children with defects in their coagulation system. Until today the standard treatment of Hemophilia A and VWD involves frequent intravenous infusions of preparations of FVIII and VWF concentrates.

These replacement therapies are generally effective, however, for example in severe hemophilia A patients undergoing prophylactic treatment Factor VIII has to be administered intravenously (i.v.) about 3 times per week due to the short plasma half life of Factor VIII of about 12 hours. Already by achieving FVIII levels above 1% of normal human plasma corresponding to a raise of FVIII levels by 0.01 U/ml, severe hemophilia A is turned into moderate hemophilia A. In prophylactic therapy the dosing regime is designed such that the trough levels of FVIII activity do not fall below levels of 2-3% of the FVIII activity of non-hemophiliacs.

The administration of a Factor VIII via intravenous administration is cumbersome, associated with pain and entails the risk of an infection especially as this is mostly done in home treatment by the patients themselves or by the parents of children being diagnosed for hemophilia A. In addition, frequent intravenous injections inevitably result in scar formation, interfering with future infusions As prophylactic treatment in severe hemophilia is started early in life, with children often being less than 2 years old, it is even more difficult to inject FVIII 3 times per week into the veins of such small patients. For a limited period of time, implantation of port systems may offer an alternative. However, in these cases repeated infections may occur and ports can cause inconvenience during physical exercise.

Thus there is a great medical need to obviate the need to infuse Factor VIII intravenously.

Subcutaneous administration has been proposed for Factor VIII, e.g. in WO 95/01804 A1 and WO 95/026750. However, very high doses of Factor VIII had to be administered to achieve an acceptable bioavailability.

Another approach to improve the bioavailability upon non-intravenous administration has been to use albumin-fused Factor VIII (WO 2011/020866 A2).

WO 2010/077297 A1 and WO 2010/077297 A1 teach the use of hyaluronidase as a spreading or dispersing agent to promote, enhance or increase the dispersion and delivery of a vast number of agents, drugs and proteins to improve the pharmacokinetic and pharmacodynamic profile of the co-administered agent, drug or protein.

It is highly desirable to improve the bioavailability of Factor VIII upon non-intravenous administration. The inventors of this application surprisingly found that the bioavailability of Factor VIII is substantially increased if it is administered in combination with a sulfated glycosaminoglycan and a hyaluronidase.

SUMMARY OF THE INVENTION

In a first aspect, the present invention therefore relates to a pharmaceutical preparation comprising at least one Factor VIII, at least one sulfated glycosaminoglycan, and at least one hyaluronidase.

In a preferred embodiment of the first aspect of the invention, the pharmaceutical preparation comprises Factor VIII, at least one sulfated glycosaminoglycan (e.g. heparin), and at least one hyaluronidase. More preferably, the pharmaceutical preparation comprises human Factor VIII, unfractionated heparin and human hyaluronidase. The Factor VIII may or may not be complexed with VWF.

In a second aspect, the invention relates to a Factor VIII for use in the treatment or prophylaxis of a bleeding disorder, wherein said treatment or prophylaxis comprises administration of at least one sulfated glycosaminoglycan and at least one hyaluronidase. In a variation of the second aspect, the invention pertains to Factor VIII, a sulfated glycosaminoglycan, and a hyaluronidase for use in the treatment or prophylaxis of a bleeding disorder.

A preferred embodiment of the second aspect of the invention is Factor VIII for use in the treatment or prophylaxis of a bleeding disorder, wherein said treatment or prophylaxis comprises administration of at least one sulfated glycosaminoglycan and at least one hyaluronidase. More preferably, the treatment or prophylaxis comprises administration of Factor VIII, heparin (e.g. unfractionated heparin) and human hyaluronidase. The Factor VIII may or may not be complexed with VWF.

It is further preferred that the bleeding disorder is hemophilia A, and that the therapy or prophylaxis comprises non-intravenous administration of the medicament, most preferably by subcutaneous, intramuscular or intradermal injection.

A third aspect of the invention is the combined use of at least one sulfated glycosaminoglycan and at least one hyaluronidase for improving the bioavailability of one or more Factor VIII. The preferred embodiments of the third aspect correspond to those of the first and second aspect mutatis mutandis.

A fourth aspect of the invention is a method of treating a bleeding disorder by administering to a subject in need thereof a therapeutically effective amount of at least one Factor VIII, at least one sulfated glycosaminoglycan and at least one hyaluronidase. Factor VIII, the sulfated glycosaminoglycan and the hyaluronidase may be administered simultaneously, e.g. mixed in a single composition. Alternatively, one component may be administered separately, while the other two components are administered jointly. In another embodiment, all three components are administered separately, e.g. in a timely staggered manner.

In yet another aspect, the present invention relates to a pharmaceutical kit comprising at least one Factor VIII, at least one sulfated glycosaminoglycan, and at least one hyaluronidase.

In all aspects of the invention, the Factor VIII is preferably human Factor VIII. A preferred sulfated glycosaminoglycan is heparin, most preferably unfractionated heparin.

DESCRIPTION OF THE FIGURES

FIG. 1 depicts the results of Example 1. The bioavailability of FVIII is increased if a sulfated glycosaminoglycan and hyaluronidase are co-administered. The effect of the combined administration on the bioavailability of the Factor VIII is synergistic.

DETAILED DESCRIPTION

The present invention concerns the treatment and prophylaxis of bleeding disorders.

As used herein, the term "bleeding disorders" includes familial and acquired hemophilia A.

According to the first aspect of the invention a pharmaceutical preparation is provided which comprises at least one Factor VIII, at least one sulfated glycosaminoglycan, and at least one hyaluronidase.

Factor VIII may be wild-type Factor VIII or may contain mutations. The degree and location of glycosylation or other post-translation modifications may vary depending on the chosen host cells and the nature of the host cellular environment. When referring to specific amino acid sequences, posttranslational modifications of such sequences are encompassed in this application.

The terms "blood coagulation Factor VIII", "Factor VIII" and FVIII" are used interchangeably herein. "Factor VIII" includes wild type Facto VIII as well as derivatives of wild type Factor VIII having the procoagulant activity of wild type Factor VIII. Derivatives may have deletions, insertions and/or additions compared with the amino acid sequence of wild type Factor VIII. The term Factor VIII includes proteolytically processed forms of Factor VIII, e.g. the form before activation, comprising heavy chain and light chain.

The term "Factor VIII" includes any Factor VIII variants or mutants having at least 10%, preferably at least 25%, more preferably at least 50%, most preferably at least 75% of the biological activity of wild type Factor VIII. A suitable test to determine the biological activity of Factor VIII is the one stage or the two stage coagulation assay (Rizza et al. 1982. Coagulation assay of FVIII:C and FIXa in Bloom ed. The Hemophilias. N.Y. Churchchill Livingston 1992) or the chromogenic substrate FVIII:activity assay (S. Rosen, 1984. Scand J Haematol 33: 139-145, suppl.). The content of these references is incorporated herein by reference.

As non-limiting examples, Factor VIII molecules include Factor VIII mutants preventing or reducing APC cleavage (Amano 1998. Thromb. Haemost. 79:557-563), albumin-fused FVIII molecules (WO 2011/020866 A2), FVIII-Fc fusion molecules (WO 04/101740 A), Factor VIII mutants further stabilizing the A2 domain (WO 97/40145), FVIII mutants resulting in increased expression (Swaroop et al. 1997. JBC 272:24121-24124), Factor VIII mutants with reduced immunogenicity (Lollar 1999. Thromb. Haemost. 82:505-508), FVIII reconstituted from differently expressed heavy and light chains (Oh et al. 1999. Exp. Mol. Med. 31:95-100), FVIII mutants reducing binding to receptors leading to catabolism of FVIII like HSPG (heparan sulfate proteoglycans) and/or LRP (low density lipoprotein receptor related protein) (Ananyeva et al. 2001. TCM, 11:251-257), disulfide bond-stabilized FVIII variants (Gale et al., 2006. J. Thromb. Hemost. 4:1315-1322), FVIII mutants with improved secretion properties (Miao et al., 2004. Blood 103:3412-3419), FVIII mutants with increased cofactor specific activity (Wakabayashi et al., 2005. Biochemistry 44:10298-304), FVIII mutants with improved biosynthesis and secretion, reduced ER chaperone interaction, improved ER-Golgi transport, increased activation or resistance to inactivation and improved half-life (summarized by Pipe 2004. Sem. Thromb. Hemost. 30:227-237), and FVIII mutants having a deletion of all or part of the B-domain (see, e.g., WO 2004/067566 A1, WO 02/102850 A2, WO 00/24759 A1 and U.S. Pat. No. 4,868,112). Particularly preferred are FVIII molecules which are "single chain" FVIII molecules. Single chain FVIII have a deletion of all or part of the B-domain and a deletion of all or a part of the acidic a3 region, so that the cleavage site at Arg1648 (which is usually cleaved during secretion) is deleted. Single chain FVIII molecules are disclosed in, e.g., WO 2004/067566 A1; US 2002/132306 A1; Krishnan et al. (1991) European Journal of Biochemistry vol. 195, no. 3, pages 637-644; Herlitschka et al. (1998) Journal of Biotechnology, vol. 61, no. 3, pages 165-173; Donath et al. (1995) Biochem. J., vol. 312, pages 49-55.

All of these Factor VIII mutants and variants are incorporated herein by reference in their entirety.

The amino acid sequence of the mature wild type form of human VIII is shown in SEQ ID NO:2. The reference to an amino acid position of a specific sequence means the position of said amino acid in the FVIII wild-type protein and does not exclude the presence of mutations, e.g. deletions, insertions and/or substitutions at other positions in the sequence referred to. For example, a mutation in "Glu2004" referring to SEQ ID NO:2 does not exclude that in the modified homologue one or more amino acids at positions 1 through 2332 of SEQ ID NO:2 are missing. A DNA sequence encoding SEQ ID NO:1 is shown in SEQ ID NO:1.

The term "glycosaminoglycan", as used herein, refers to an oligo- or polysaccharide comprising particularly aminohexose units. Sulfated glycosaminoglycans include, but are not limited to, chondroitin sulfate, dermatan sulfate, keratan sulfate, heparin and heparan sulfate. Preferably, the sulfated glycosaminoglycan is a heparin, most preferably, the sulfated glycosaminoglycan is selected from the group consisting of unfractionated heparin, low molecular weight heparin and chondroitin sulfate.

The term "heparin" includes unfractionated heparin and heparins having a lower molecular weight. In one embodiment, the heparin used in accordance with this invention is "unfractionated heparin" which may have an average molecular weight of about 8 kDa to about 30 kDa, preferably of about 10 kDa to about 20 kDa, most preferably of about 12 kDa to about 16 kDa, e.g. about 15 kDa. In another embodiment, the heparin used in accordance with this invention is a low molecular weight heparin (LMWH). LMWHs are heparins or heparin salts having an average molecular weight of less than 8000 Da and for which at least 60% of all chains have a molecular weight less than 8000 Da. Preferably, the molecular weight of the LMWH used in accordance with this invention is about 2 kDa to about 8 kDa, more preferably about 3 kDa to about 6 kDa, most preferably of about 4 kDa to about 5 kDa, e.g. about 4.5 kDa. The LMWHs can be obtained by various methods of fractionation or depolymerisation of polymeric heparin. Examples of LMWHs include, but are not limited to, ardeparin (Normiflo), certoparin (Sandoparin), enoxaparin (Lovenox and Clexane), parnaparin (Fluxum), tinzaparin (Innohep and Logiparin), dalteparin (Fragmin), reviparin (Clivarin) and nadroparin (Fraxiparin).

The term "heparin" includes also small molecular weight fragments of heparin molecules, either derived from naturally occurring heparin by cleavage and isolation or by synthetic routes. A commercially available sulfated pentasaccharide exists for example that is manufactured synthetically and which structure is derived from heparin. It is available as Fondaparinux sodium.

Chondroitin sulfate includes, e.g., Chondroitin sulfate A (chondroitin-4-sulfate), Chondroitin sulfate C (chondroitin-6-sulfate), Chondroitin sulfate D (chondroitin-2,6-sulfate), and Chondroitin sulfate E (chondroitin-4,6-sulfate).

Dermatan sulfate (previously also called Chondroitin sulfate B) is another sulfated glycosaminoglycan which is commercially available.

Keratan sulfate is another sulfated glycosaminoglycan. The structure of keratan sulfate is described in, e.g., Funderburgh (2000) Glycobiology vol. 10 no. 10 pp. 951-958.

Heparan sulfate is an N-sulfated polysaccharide which is different from heparin (see, e.g., Gallagher, J. T., Lyon, M. (2000). "Molecular structure of Heparan Sulfate and interactions with growth factors and morphogens". In Iozzo, M, V. Proteoglycans: structure, biology and molecular interactions. Marcel Dekker Inc. New York, N.Y. pp. 27-59; and Gallagher, J. T. Walker, A. (1985). "Molecular distinctions between Heparan Sulphate and Heparin: Analysis of sulphation patterns indicates Heparan Sulphate and Heparin are separate families of N-sulphated polysaccharides". Biochem. J. 230 (3): 665-74)

The term "hyaluronidase" refers to any polypeptide having hyaluronoglucuronidase activity, hyaluronoglucosaminidase activity or hyaluronate lyase activity. Preferably, the hyaluronidase is capable of at least partially degrading hyaluronan (hyaluronic acid).

There are three classes of hyaluronidases:
(1) Mammalian hyaluronidases (EC 3.2.1.35) which are endo-beta-N-acetylhexosaminidases with tetrasaccharides and hexasaccharides as the major end products. They have both hydrolytic and transglycosidase activities, and can degrade hyaluronan and chondroitin sulfates (CS), specifically C4-S and C6-S.

(2) Bacterial hyaluronidases (EC 4.2.2.1) are endo-beta-N-acetylhexosaminidases that operate by a beta-elimination reaction that yields primarily disaccharide end products.

(3) Hyaluronidases (EC 3.2.1.36) from leeches, other parasites, and crustaceans are endo-beta-glucuronidases that generate tetrasaccharide and hexasaccharide end products through hydrolysis of the beta 1-3 linkage.

Mammalian hyaluronidases are preferred according to the invention and can be further divided into two groups: neutral active and acid active enzymes. Neutral active hyaluronidases are preferred. The hyaluronidase of the present invention may be derived from any species. More preferably, however, the hyaluronidase is a human hyaluronidase. Still more preferably, the hyaluronidases encoded by the human genes HYAL1 (Uniprot/Swissprot Acc. No. Q12794), HYAL2 (Uniprot/Swissprot Acc. No. Q12891), HYAL4 (Uniprot/Swissprot Acc. No. Q2M3T9) and PH20/SPAM1 (Uniprot/Swissprot Acc. No. P38567), respectively, are used as the hyaluronidase in the present invention. Most preferably, the hyaluronidase is human PH20 (Uniprot/Swissprot Acc. No. P38567). Particularly preferred are further the soluble PH20 polypeptides and the extended soluble PH20 polypeptides described in WO 2010/077294 A1 (see in particular, the amino acid sequence of human PH20 depicted in FIG. 1 of WO 2010/077294 A1). These polypeptides are incorporated herein by reference.

Further included are any variants and mutants of the above-described hyaluronidases, as long as they still have at least some hyaluronidase activity.

As used herein, hyaluronidase activity refers to the ability to enzymatically catalyze the cleavage of hyaluronic acid. The United States Pharmacopeia (USP) XXII assay for hyaluronidase determines hyaluronidase activity indirectly by measuring the amount of higher molecular weight hyaluronic acid, or hyaluronan, (HA) substrate remaining after the enzyme is allowed to react with the HA for 30 min at 37° C. (USP XXII-NF XVII (1990) 644-645 United States Pharmacopeia Convention, Inc, Rockville, Md.). A Reference Standard solution can be used in an assay to ascertain the relative activity, in units, of any hyaluronidase. In vitro assays to determine the hyaluronidase activity of hyaluronidases are known in the art. Exemplary assays include the microturbidity assay that measures cleavage of hyaluronic acid by hyaluronidase indirectly by detecting the insoluble precipitate formed when the uncleaved hyaluronic acid binds with serum albumin (see e.g. Hynes, W. L., J. J. Ferretti (1994). Assays for hyaluronidase activity. *Meth Enzymol* 235: 606-616). Reference Standards can be used, for example, to generate a standard curve to determine the activity in Units of the hyaluronidase being tested. In another example, hyaluronidase activity is measured using a microtiter assay in which residual biotinylated hyaluronic acid is measured following incubation with hyaluronidase (see e.g. Frost and Stern (1997) Anal. Biochem. 251:263-269, U.S. Patent Publication No. 2005/0260186). Other assays to measure hyaluronidase activity also are known in the art and can be used (see e.g. Deipech et al., (1995) Anal. Biochem. 229:35-41; Takahashi et al., (2003) Anal. Biochem. 322:257-263).

In one embodiment, the Factor VIII, the sulfated glycosaminoglycan, and the hyaluronidase are contained in the same composition. This composition comprising the three components may be administered to the patient by a single injection or the like.

In another embodiment, the Factor VIII, the sulfated glycosaminoglycan, and the hyaluronidase are not present in the same composition. For example, each of the three components may be provided in a separate dosage form in said pharmaceutical preparation. Alternatively, two of the three components may be present in the same composition, while the third component is provided in a separate dosage form. In yet another variation, each of the three components is provided in a separate dosage form in said pharmaceutical preparation. In summary, the present invention encompasses the following embodiments.

TABLE 1

| Embodiment | The pharmaceutical preparation or the kit comprises: |
|---|---|
| 1 | a composition comprising the Factor VIII, the sulfated glycosaminoglycan, and the hyaluronidase (in admixture) |
| 2 | a first composition comprising the Factor VIII and the sulfated glycosaminoglycan, and a second composition comprising the hyaluronidase. |
| 3 | a first composition comprising the Factor VIII and the hyaluronidase, and a second composition comprising the sulfated glycosaminoglycan. |
| 4 | a first composition comprising the Factor VIII, and a second composition comprising the sulfated glycosaminoglycan and the hyaluronidase. |
| 5 | a first composition comprising the Factor VIII, a second composition comprising the sulfated glycosaminoglycan, and a third composition comprising the hyaluronidase. |

If the three components are not present in the same composition, as in embodiments (1) to (4) of table 1, the separate compositions may either be administered separately, or they may be mixed shortly before administration so that all three components will be administered simultaneously. If there is separate administration, the administration may be done sequentially, e.g. in a time-staggered manner. When the administration is done separately, the order of the administration may be such that the Factor VIII is administered first, followed by the administration of sulfated glycosaminoglycan and the hyaluronidase. Alternatively, the sulfated glycosaminoglycan may be administered as first component, followed by administration of the Factor VIII and the hyaluronidase. In yet another embodiment, the hyaluronidase is administered first, followed by administration of the Factor VIII and the sulfated glycosaminoglycan. The time between the administration of the three components may vary, e.g. from about 1 second to about 24 hours, or from about 10 seconds to about 1 hour, or from about 20 seconds to about 10 minutes. Typically, the three components are administered within 24 or less, preferably within 1 hour or less, most preferably within 10 minutes or less. In general, it is preferred that the three components are administered simultaneously by a single administration, e.g. injection. Various routes of administration are discussed below. They apply to the above mutatis mutandis.

The components of the pharmaceutical preparation may be dissolved in conventional physiologically compatible aqueous buffer solutions to which there may be added, optionally, pharmaceutical excipients to provide the pharmaceutical preparation.

Such pharmaceutical carriers and excipients as well as the preparation of suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", 3$^{rd}$ edition, Kibbe et al., Pharmaceutical Press (2000)). In certain embodiments, a pharmaceutical composition can comprise at least one additive such as a filler, bulking agent, buffer, stabilizer, or excipient. Standard pharmaceutical formulation techniques are well known to persons skilled in the art (see, e.g., 2005 Physicians' Desk Reference®, Thomson Healthcare: Montvale, N.J., 2004; Remington: The Science and Practice of Pharmacy, 20th ed., Gennaro et al., Eds. Lippincott Williams & Wilkins: Philadelphia, Pa., 2000). Suitable pharmaceutical additives include, e.g., sugars like mannitol, sorbitol, lactose, sucrose, trehalose, or others, amino acids like histidine, arginine, lysine, glycine, alanine, leucine, serine, threonine, glutamic acid, aspartic acid, glutamine, asparagine, phenylalanine, or others, additives to achieve isotonic conditions like sodium chloride or other salts, stabilizers like Polysorbate 80, Polysorbate 20, Polyethylene glycol, propylene glycol, calcium chloride, or others, physiological pH buffering agents like Tris(hydroxymethyl)aminomethan, and the like. In certain embodiments, the pharmaceutical compositions may contain pH buffering reagents and wetting or emulsifying agents. In further embodiments, the compositions may contain preservatives or stabilizers. In particular, the pharmaceutical preparation comprising the Factor VIII may be formulated in lyophilized or stable soluble form. The Factor VIII may be lyophilized by a variety of procedures known in the art. Also if the sulfated glycosaminoglycan and the Factor VIII are contained in the same composition, such composition may also be provided in lyophilized or in stable soluble form. Lyophilized formulations are reconstituted prior to use by the addition of one or more pharmaceutically acceptable diluents such as sterile water for injection or sterile physiological saline solution or a suitable buffer solution.

The composition(s) contained in the pharmaceutical preparation of the invention may be delivered to the individual by any pharmaceutically suitable means. Various delivery systems are known and can be used to administer the composition by any convenient route. Preferably, the composition(s) contained in the pharmaceutical preparation of the invention are delivered to the individual by non-intravenous administration. More preferably, the composition(s) of the invention are formulated for subcutaneous, intramuscular, intraperitoneal, intracerebral, intrapulmonar, intranasal or transdermal administration, most preferably for subcutaneous, intramuscular or transdermal administration according to conventional methods. The formulations can be administered continuously by infusion or by bolus injection. Some formulations encompass slow release systems.

The composition(s) of the pharmaceutical preparation of the present invention is/are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

In one embodiment of the invention, the plasma level of the Factor VIII in the treated subject is, during a period from 5 hours after subcutaneous injection to 8 hours after subcutaneous injection, continuously higher than 2%, preferably higher than 5%, more preferably higher than 8%, most preferably higher than 10%, of the normal plasma level of the Factor VIII in healthy subjects. The plasma level is to be determined as shown hereinafter in Example 1.

In one embodiment of the invention, the plasma level of the Factor VIII in the treated subject is, during a period from 4 hours after subcutaneous injection to 16 hours after subcutaneous injection, continuously higher than 2%, preferably higher than 5%, more preferably higher than 8%, most preferably higher than 10%, of the normal plasma level of the Factor VIII in healthy subjects.

In another embodiment of the invention, the plasma level of the Factor VIII in the treated subject is, during a period from 3 hours after subcutaneous injection to 24 hours after subcutaneous injection, continuously higher than 2%, preferably higher than 4%, more preferably higher than 6%, most preferably higher than 8%, of the normal plasma level of the Factor VIII in healthy subjects.

In another embodiment of the invention, the plasma level of the Factor VIII in the treated subject is, during a period from 2 hours after subcutaneous injection to 32 hours after subcutaneous injection, continuously higher than 2%, preferably higher than 3%, more preferably higher than 4%, most preferably higher than 5%, of the normal plasma level of the Factor VIII in healthy subjects.

In yet another embodiment of the invention, the plasma level of the Factor VIII in the treated subject is, during a period from 1 hour after injection to 48 hours after injection, continuously higher than 2%, preferably higher than 3%, more preferably higher than 4%, most preferably higher than 5%, of the normal plasma level of the Factor VIII in healthy subjects.

The dose of Factor VIII for one administration is typically less than 1,000 IU/kg body weight, or less than 800 IU/kg body weight, or less than 600 IU/kg body weight, or less than 400 IU/kg body weight, e.g. at a dose of from about 10 IU/kg body weight to about 1,000 IU/kg body weight, or from about 20 IU/kg body weight to about 800 IU/kg body weight, or from about 30 IU/kg body weight to about 700 IU/kg body weight, or from about 40 IU/kg body weight to about 600 IU/kg body weight, or from about 50 IU/kg body weight to about 500 IU/kg body weight, or from about 75 IU/kg body weight to about 400 IU/kg body weight, or from about 100 IU/kg body weight to about 300 IU/kg body weight, or from about 50 IU/kg body weight to about 1,000 IU/kg body weight, or from about 50 IU/kg body weight to about 800 IU/kg body weight, or from about 50 IU/kg body weight to about 700 IU/kg body weight, or from about 50 IU/kg body weight to about 600 IU/kg body weight, or from about 50 IU/kg body weight to about 500 IU/kg body weight, or from about 50 IU/kg body weight to about 400 IU/kg body weight, or from about 50 IU/kg body weight to about 300 IU/kg body weight, or about 50 IU/kg body weight to about 200 IU/kg body weight. The FVIII can be administered on its own, or as a complex with VWF.

The amount of sulfated glycosaminoglycans administered typically ranges from about 0.01 to about 100 mg/kg body weight, from about 0.05 to about 10 mg/kg body weight, from about 0.1 to about 5 mg/kg body weight, from about 0.25 to about 2 mg/kg body weight, or from about 0.5 to about 1 mg/kg body weight. The amount of sulfated glycosaminoglycan may range from about 0.001 to about 100 mg/mL product applied, from about 0.01 to about 10 mg/mL product applied, from about 0.05 to about 1 mg/mL product applied.

Typically, a therapeutically effective dose of the hyaluronidase is from about 1 to about 10,000 U/kg body weight, from about 3 to about 5,000 U/kg body weight, from about 5 to about 1,000 U/kg body weight, from about 8 to about 500 U/kg body weight, or from about 10 to about 250 U/kg body weight, in a stabilized solution or suspension or a lyophilized from. The formulations can be provided in unit-dose forms such as, but not limited to, ampoules, syringes and individually packaged tablets or capsules. For example, a hyaluronidase can be administered subcutaneously at about 10 U, 25 U, 50 U, 100 U, 250 U, 500 U, 1000 U, 5,000 U or more. The hyaluronidase can be administered separately (from the Factor VIII and the sulfated glycosaminoglycan), or simultaneously with the Factor VIII and the sulfated glycosaminoglycan, optionally with other pharmacologically effective agent or therapeutic agent in a total volume of 0.1-50 ml, 0.5-20 ml, or 1-10 ml, typically 1-10 ml. Typically, volumes of injections or infusions of a hyaluronidase contemplated herein are from at or about 0.01 mL, 0.05 mL, 0.1 mL, 0.2 mL, 0.3 mL, 0.4 mL, 0.5 mL, 1 mL, 2 mL, 3 mL, 5 mL, 10 ml, 25 ml, 50 ml or more. In some examples, dosages can be provided as a ratio of amount of hyaluronidase to Factor VIII administered. The ratio of Units hyaluronidase to U Factor VIII may range from about 50:1 to about 1:50, or from about 10:1 to about 1:10, or from about 5:1 to about 1:5. The hyaluronidase can be provided as a stock solution at or about 100 U/ml, 150 U/ml, 200 U/ml, 300 U/ml, 400 U/ml, 500 U/mL, 600 U/mL, 800 U/mL or 1000 U/mL, or can be provided in a more concentrated form, for example at or about 2000 U/ml, 3000 U/ml, 4000 U/ml, 5000 U/ml, 8000 U/ml, 10,000 U/mL or 20,000 U/mL for use directly or for dilution to the effective concentration prior to use. The hyaluronidase can be provided as a liquid or lyophilized formulation.

The term "bioavailability", as used herein, refers to the proportion of an administered dose of a Factor VIII (e.g. Factor VIII or a FVIII-related preparation) that can be detected in plasma at predetermined times until a final time point after subcutaneous, intravenous or intradermal administration. Typically, bioavailability is measured in test animals by administering a dose of between 10 IU/kg and 1000 IU/kg of the preparation (e.g. at 400 IU/kg body weight); obtaining plasma samples at pre-determined time points after administration; and determining the content of the Factor VIII, e.g. Factor VIII or Factor VIII-related polypeptides in the samples using one or more of a chromogenic or clotting assay (or any bioassay), an immunoassay, or an equivalent thereof. The bioavailability is expressed as the area under the curve (AUC) of the concentration or activity of the Factor VIII in plasma on the y-axis and the time after administration on the x-axis until a predefined final time point after administration. Preferably, this predefined time point is 48 hours after administration. Most preferably, the bioavailability is determined as shown in Example 1 herein below. Relative bioavailability of a test preparation refers to the ratio between the AUC of the test preparation and that of the reference preparation which is administered in the same dose and way (e.g. intravenous, subcutaneous or intradermal) as the test preparation.

According to the present invention, the bioavailability of the Factor VIII (when co-administered with the sulfated glycosaminoglycan and the hyaluronidase) is higher than that of the Factor VIII when administered alone. Preferably, the bioavailability is increased by at least 100%, more preferably by at least 200%, more preferably by at least 300%, most preferably by at least 400%. The increase in bioavailability is preferably obtained when the Factor VIII is administered by subcutaneous injection at a dose of less than 1,000 IU/kg body weight, or less than 800 IU/kg body weight, or less than 600 IU/kg body weight, or less than 400 IU/kg body weight, e.g. at a dose of from about 10 IU/kg body weight to about 1,000 IU/kg body weight, or from about 20 IU/kg body weight to about 800 IU/kg body weight, or from about 30 IU/kg body weight to about 700 IU/kg body weight, or from about 40 IU/kg body weight to about 600 IU/kg body weight, or from about 50 IU/kg body weight to about 500 IU/kg body weight, or from about 75 IU/kg body weight to about 400 IU/kg body weight, or from about 100 IU/kg body weight to about 300 IU/kg body weight, or from about 50 IU/kg body weight to about 1,000 IU/kg body weight, or from about 50 IU/kg body weight to about 800 IU/kg body weight, or from about 50 IU/kg body weight to about 700 IU/kg body weight, or from about 50 IU/kg body weight to about 600 IU/kg body weight, or from about 50 IU/kg body weight to about 500 IU/kg body weight, or from about 50 IU/kg body weight to about 400 IU/kg body weight, or from about 50 IU/kg body weight to about 300 IU/kg body weight, or about 50 IU/kg body weight to about 200 IU/kg body weight. The Factor VIII can be administered on its own, or as a complex with VWF.

The pharmaceutical composition(s) of the invention may be administered alone or in conjunction with other therapeutic agents. These agents may be incorporated as part of the same pharmaceutical.

EXAMPLES

Example 1

Assessment of bioavailability of s.c. Applied FVIII and Various Additives in a Hemophilia A Model Materials and Animal Model The Factor VIII used in the experiments was a B-domain truncated, single-chain recombinant factor VIII (hereinafter referred to as "rFVIII"). It has a deletion of most of the B domain and part of the acidic a3 region of the wild type Factor VIII sequence. This Factor VIII is a "single chain" Factor VIII generated by fusing Asn764 with Thr1653. It has been expressed in cell culture cells and purified from the cell culture medium.

The further agents used are summarized in Table 2.

TABLE 2

| Compound class | Type of compound and/or source |
|---|---|
| Heparin | Unfractionated heparin (Heparin-Natrium-25000-ratiopharm) |
| Hyaluronidase | Bovine Hyaluronidase |

Factor VIII knockout mice were used as animal model for hemophilia A. These mice lack exons 16 and 17 and thus do not express FVIII (Bi L. et al, Nature genetics, 1995, Vol 10(1), 119-121; Bi L. et al, Blood, 1996, Vol 88(9), 3446-3450). This allows the analysis of FVIII levels following treatment by quantification of FVIII activity in the plasma of the ko mice.

Methods

To assess whether extravascular injections might be an option for an improved therapy with FVIII (human) a typical representative for an extravascular therapy, subcutaneous injection was chosen. The design of the non-clinical pharmacokinetic study performed is detailed in table 3 below. Plasma levels of Factor VIII activity were determined following a single intravenous or subcutaneous injection of FVIII together with various additives (detailed treatment groups in table 3) into a hemophilia A model.

Corresponding groups were treated with the same dose of FVIII (chromogenic substrate (CS) activity assay) in the presence of various different additives. For a single application the various different components for each treatment group were mixed together in a volume of 200 μL (identical volumes for all groups) prior to subcutaneous application to FVIII knockout (ko) mice weighing about 25 g. The treatment groups are summarized in table 3.

Under short term anesthesia, blood samples were drawn, anticoagulated using sodium citrate to 10% citrate blood, processed to plasma and stored at −70° C. for the determination of FVIII activity. The sampling time points are detailed in table 4. Quantification of FVIII activity in plasma was performed by a standard, aPTT based approach (Behring Coagulation Timer). The animals were kept at standard housing conditions.

TABLE 3

Treatment groups

| No. | Treatment | FVIII (CS activity assay)/ Additive Dose | volume [mL/kg] | schedule | route | N |
|---|---|---|---|---|---|---|
| 1 | FVIII | 400 IU/kg | 8 | single injection (t = 0) | s.c. | 25 |
| 2 | FVIII/ Heparin | 400 IU/kg/ 40 U/kg (5 U/mL product applied) | 8 | single injection | s.c. | 25 |
| 3 | FVIII/ Hyaluronidase | 400 IU/kg/ 200 U/kg | 8 | single injection | s.c. | 20 |
| 4 | FVIII/ Heparin/ Hyaluronidase | 400 IU/kg/ 40 U/kg (5 U/mL product applied)/ 200 U/kg | 8 | single injection | s.c. | 20 |

Results

The results are summarized in Table 4 and FIG. 1. Subcutaneous injection of 400 IU/kg FVIII in presence of heparin or hyaluronidase to FVIII ko mice resulted in a significant increase of FVIII activity in plasma level as compared to administration of FVIII alone. When heparin and hyaluronidase were co-administered with FVIII, there was even a synergistic increase in bioavailability.

TABLE 4

FVIII activity in % of the FVIII activity in normal human plasma

| Time-point (h) | FVIII 400 IU/kg s.c. | FVIII 400 IU/kg/ Heparin 40 U/kg s.c. | FVIII/ Hyaluronidase s.c | FVIII/ Heparin/ Hyaluronidase s.c. |
|---|---|---|---|---|
| 0.5 | 1.02 ± 0.8 | 52.90 ± 2.70 | 4.90 ± 2.61 | 8.23 ± 3.39 |
| 2 | 13.04 ± 3.90 | 15.16 ± 4.12 | 12.70 ± 9.23 | 41.75 ± 27.45 |
| 5 | 1.15 ± 1.28 | 26.66 ± 5.74 | 21.42 ± 4.40 | 37.57 ± 12.24 |
| 8 | 2.32 ± 2.27 | 15.56 ± 4.22 | 10.08 ± 5.40 | 53.89 ± 13.86 |
| 16 | 4.82 ± 2.35 | 12.08 ± 2.35 | 10.34 ± 4.25 | 16.45 ± 3.73 |
| 24 | 9.72 ± 8.09 | 14.10 ± 3.76 | 6.46 ± 2.91 | 16.57 ± 7.66 |
| 32 | 2.48 ± 2.20 | 10.84 ± 5.31 | 7.08 ± 2.14 | 12.39 ± 6.41 |
| 48 | 1.15 ± 1.72 | 7.02 ± 1.24 | 3.32 ± 2.09 | 10.01 ± 4.74 |
| AUC 0-48 h (h × % of the norm SHP) | 202.0 | 598.4 | 399.3 | 1034.0 |

The peak values are shaded in grey.

Example 2

Assessment of Bioavailability of s.c. Applied Factor VIII and Human Hyaluronidase PH20 in a Hemophilia A Model The soluble form of human Hyaluronidase PH20 may be purchased from Halozyme. Alternatively, it may be prepared as described in WO 2010/077297 A1.

The other agents to be used are identical to those used in Example 1.

The experiment can be carried out as described above in Example 1. A possible outline of the treatment groups is as follows:

TABLE 4

Treatment groups

| No. | Treatment | FVIII: chromogen/ Additive Dose | volume [mL/kg] | schedule | route | N |
|---|---|---|---|---|---|---|
| 1 | FVIII | 400 IU/kg | 8 | single injection (t = 0) | s.c. | 25 |
| 2 | FVIII/ Heparin | 400 IU/kg/ 40 U/kg (5 U/mL) | 8 | single injection | s.c. | 25 |
| 3 | FVIII/ Hyaluronidase PH20 | 400 IU/kg/ 200 U/kg | 8 | single injection | s.c. | 20 |
| 4 | FVIII/ Heparin/ Hyaluronidase PH20 | 400 IU/kg/ 40 U/kg (5 U/mL)/ 200 U/kg | 8 | single injection | s.c. | 20 |

The results can be displayed in the same manner as for Example 1 above.

The invention claimed is:

1. A pharmaceutical preparation comprising Factor VIII, a sulfated glycosaminoglycan, and a hyaluronidase, wherein the Factor VIII, the sulfated glycosaminoglycan, and the hyaluronidase are present in a single composition at dosages sufficient to increase the bioavailability of Factor VIII after non-intravenous administration relative to the bioavailability when the same amount of Factor VIII is administered non-intravenously without the sulfated glycosaminoglycan and the hyaluronidase.

2. The pharmaceutical preparation of claim 1, wherein the Factor VIII is provided at a dosage ranging from about 10 IU/kg body weight to about 1,000 IU/kg body weight, the sulfated glycosaminoglycan is provided at a dosage ranging from about 0.01 mg/kg body weight to about 100 mg/kg body weight, and the hyaluronidase is provided at a dosage ranging from about 1 U/kg body weight to about 10,000 U/kg body weight.

3. The pharmaceutical preparation of claim 1, wherein the hyaluronidase is a human hyaluronidase.

4. The pharmaceutical preparation of claim 1, wherein the sulfated glycosaminoglycan is a heparin.

5. The pharmaceutical preparation of claim 4, wherein the heparin is unfractionated heparin.

* * * * *